(12) United States Patent
Steiner et al.

(10) Patent No.: US 6,943,187 B2
(45) Date of Patent: Sep. 13, 2005

(54) PYRROLIDINE DERIVATIVE HAIR GROWTH COMPOSITIONS AND USES

(75) Inventors: Joseph P. Steiner, Finksburg, MD (US); Gregory S. Hamilton, Catonsville, MD (US)

(73) Assignee: GPI Nil Holdings, Inc., Wilmington, DE (US)

( * ) Notice: Subject to any disclaimer, the term of this patent is extended or adjusted under 35 U.S.C. 154(b) by 167 days.

(21) Appl. No.: 10/147,944

(22) Filed: May 20, 2002

(65) Prior Publication Data

US 2002/0198250 A1 Dec. 26, 2002

Related U.S. Application Data

(63) Continuation of application No. 09/893,567, filed on Jun. 29, 2001, now abandoned, which is a continuation-in-part of application No. 09/089,416, filed on Jun. 3, 1998, now abandoned, which is a continuation-in-part of application No. 08/869,426, filed on Jun. 4, 1997, now Pat. No. 5,945,441.

(51) Int. Cl.[7] .................................................. A61K 31/40
(52) U.S. Cl. ...................... 514/423; 514/277; 514/336; 514/342; 514/343; 514/427; 514/880
(58) Field of Search ................................. 514/423, 277, 514/336, 343, 427, 342, 880

(56) References Cited

U.S. PATENT DOCUMENTS

| | | | |
|---|---|---|---|
| 4,310,461 A | 1/1982 | Krapcho et al. | |
| 4,374,829 A | 2/1983 | Harris et al. | |
| 4,390,695 A | 6/1983 | Krapcho et al. | |
| 4,438,031 A | 3/1984 | Winkley et al. | |
| 4,531,964 A | 7/1985 | Shimano et al. | |
| 4,574,079 A | 3/1986 | Gavras et al. | |
| 4,578,474 A | 3/1986 | Krapcho et al. | |
| 4,593,102 A | 6/1986 | Shanklin, Jr. | |
| 4,808,573 A | 2/1989 | Gold et al. | |
| 4,818,749 A | 4/1989 | Gold et al. | |
| 4,996,193 A | 2/1991 | Hewitt et al. | |
| 5,015,470 A | * 5/1991 | Gibson ........................ 514/2 |
| 5,147,877 A | 9/1992 | Goulet | |
| 5,189,042 A | 2/1993 | Goulet et al. | |
| 5,192,773 A | 3/1993 | Armistead et al. | |
| 5,208,241 A | 5/1993 | Ok et al. | |
| 5,252,579 A | 10/1993 | Skotnicki et al. | |
| 5,258,389 A | 11/1993 | Goulet et al. | |
| 5,284,826 A | 2/1994 | Eberle | |
| 5,284,840 A | 2/1994 | Rupprecht et al. | |
| 5,284,877 A | 2/1994 | Organ et al. | |
| 5,292,747 A | 3/1994 | Davis et al. | |
| 5,294,603 A | 3/1994 | Rinehart | |
| 5,319,098 A | 6/1994 | Burbaum et al. | |
| 5,330,993 A | 7/1994 | Armistead et al. | |
| 5,342,625 A | 8/1994 | Hauer et al. | |
| 5,359,138 A | 10/1994 | Takeuchi et al. | |
| 5,385,908 A | 1/1995 | Nelson et al. | |
| 5,385,918 A | 1/1995 | Connell et al. | |
| 5,414,083 A | 5/1995 | Hackl et al. | |
| 5,424,454 A | 6/1995 | Burbaum et al. | |
| 5,447,915 A | 9/1995 | Schreiber et al. | |
| 5,457,111 A | 10/1995 | Luly et al. | |
| 5,470,878 A | 11/1995 | Michnick et al. | |
| 5,472,687 A | 12/1995 | Proctor | |
| 5,506,228 A | 4/1996 | Norton et al. | |
| 5,516,797 A | 5/1996 | Armistead et al. | |
| 5,532,248 A | 7/1996 | Goulet et al. | |
| 5,543,423 A | 8/1996 | Zelle et al. | |
| 5,574,011 A | * 11/1996 | Tien ........................... 514/14 |
| 5,614,547 A | 3/1997 | Hamilton et al. | |
| 5,620,971 A | 4/1997 | Armistead et al. | |
| 5,631,017 A | 5/1997 | Sharpe et al. | |
| 5,703,088 A | 12/1997 | Sharpe et al. | |
| 5,714,510 A | 2/1998 | Proctor | |
| 5,801,197 A | 9/1998 | Steiner et al. | |
| 5,846,979 A | 12/1998 | Hamilton et al. | |
| 5,859,031 A | 1/1999 | Hamilton et al. | |
| 5,945,441 A | 8/1999 | Steiner et al. | |
| 6,004,993 A | 12/1999 | Steiner et al. | |
| 6,054,452 A | 4/2000 | Hamilton et al. | |
| 6,172,087 B1 | 1/2001 | Steiner et al. | |
| 6,177,455 B1 | 1/2001 | Steiner et al. | |
| 6,187,784 B1 | 2/2001 | Steiner et al. | |
| 6,187,796 B1 | 2/2001 | Steiner et al. | |
| 6,187,806 B1 | 2/2001 | Steiner et al. | |
| 6,191,125 B1 | 2/2001 | Steiner et al. | |
| 6,194,440 B1 | 2/2001 | Steiner et al. | |
| 6,218,423 B1 | 4/2001 | Ross et al. | |

(Continued)

FOREIGN PATENT DOCUMENTS

| | | |
|---|---|---|
| DE | DT 2505114 | 8/1976 |
| DE | 3508251 | 9/1986 |
| DE | 3931051 | 3/1990 |
| DE | 4015255 | 11/1991 |
| EP | 12401 | 6/1980 |
| EP | 48159 | 3/1982 |
| EP | 50800 | 5/1982 |
| EP | 73143 | 3/1983 |
| EP | 88350 | 9/1983 |
| EP | 196841 | 10/1986 |
| EP | 260118 | 3/1988 |
| EP | 333174 | 9/1989 |
| EP | 352000 | 1/1990 |
| EP | 378318 | 7/1990 |
| EP | 0420707 | 8/1990 |
| EP | 0471135 | 8/1990 |
| EP | 405994 | 1/1991 |

(Continued)

OTHER PUBLICATIONS

CA111:12332, Unilever, JP 19880711, abstract.*
CA126:37059, Tien, US 5574011, abstract.*

(Continued)

Primary Examiner—Rebecca Cook
(74) Attorney, Agent, or Firm—Foley & Lardner LLP

(57) ABSTRACT

This invention relates to pharmaceutical compositions and methods for treating alopecia and promoting hair growth using pyrrolidine derivatives.

15 Claims, 5 Drawing Sheets

U.S. PATENT DOCUMENTS

| | | | |
|---|---|---|---|
| 6,239,164 B1 | 5/2001 | Steiner et al. |
| 6,251,892 B1 | 6/2001 | Hamilton et al. |
| 6,271,244 B1 | 8/2001 | Steiner et al. |
| 6,274,602 B1 | 8/2001 | Steiner et al. |
| 6,274,617 B1 | 8/2001 | Steiner et al. |
| 6,294,551 B1 | 9/2001 | Hamilton et al. |
| 6,331,537 B1 | 12/2001 | Hamilton et al. |
| 2001/0029261 A1 | 10/2001 | Steiner et al. |
| 2001/0029263 A1 | 10/2001 | Steiner et al. |
| 2001/0034362 A1 | 10/2001 | Ross et al. |
| 2001/0036942 A1 | 11/2001 | Hamilton et al. |
| 2001/0036947 A1 | 11/2001 | Steiner et al. |
| 2001/0036952 A1 | 11/2001 | Steiner et al. |
| 2001/0041733 A1 | 11/2001 | Steiner et al. |
| 2002/0010205 A1 | 1/2002 | Stainer et al. |
| 2002/0016341 A1 | 2/2002 | Steiner et al. |
| 2002/0028814 A1 | 3/2002 | Wu et al. |
| 2002/0037924 A1 | 3/2002 | Steiner et al. |
| 2002/0045641 A1 | 4/2002 | Hamilton et al. |
| 2002/0045647 A1 | 4/2002 | Steiner et al. |
| 2002/0058685 A1 | 5/2002 | Hamilton |

FOREIGN PATENT DOCUMENTS

| | | |
|---|---|---|
| EP | 419049 | 3/1991 |
| EP | 423714 | 4/1991 |
| EP | 0443983 | 12/1991 |
| EP | 0494005 | 12/1991 |
| EP | 468339 | 1/1992 |
| EP | 0519819 | 6/1992 |
| EP | 564924 | 10/1993 |
| EP | 572365 | 12/1993 |
| EP | 652229 | 5/1995 |
| EP | 0823419 | 8/1997 |
| GB | 2247456 | 3/1992 |
| JP | 04149166 | 5/1992 |
| JP | 05178824 | 7/1993 |
| WO | WO 8800040 | 1/1988 |
| WO | WO8809789 | 12/1988 |
| WO | WO 8906234 | 7/1989 |
| WO | WO9012805 | 11/1990 |
| WO | WO9104985 | 4/1991 |
| WO | WO9113088 | 9/1991 |
| WO | WO9200278 | 1/1992 |
| WO | WO9203472 | 3/1992 |
| WO | WO9204370 | 3/1992 |
| WO | WO9216501 | 10/1992 |
| WO | WO9218478 | 10/1992 |
| WO | WO9219593 | 11/1992 |
| WO | WO9219745 | 11/1992 |
| WO | WO9221313 | 12/1992 |
| WO | WO9307269 | 4/1993 |
| WO | WO9313066 | 7/1993 |
| WO | WO 9314072 | 7/1993 |
| WO | WO 9314762 | 8/1993 |
| WO | WO 9318736 | 9/1993 |
| WO | WO9323548 | 11/1993 |
| WO | WO9325546 | 12/1993 |
| WO | WO 9403476 | 2/1994 |
| WO | WO9405639 | 3/1994 |
| WO | WO9407858 | 4/1994 |
| WO | WO9413629 | 6/1994 |
| WO | WO 9502684 | 1/1995 |
| WO | WO 9512398 | 5/1995 |
| WO | WO9512572 | 5/1995 |
| WO | WO9524385 | 9/1995 |
| WO | WO9526337 | 10/1995 |
| WO | WO 9611943 | 10/1995 |
| WO | WO 9534303 | 12/1995 |
| WO | WO9535308 | 12/1995 |
| WO | WO9535367 | 12/1995 |
| WO | WO9606097 | 2/1996 |
| WO | WO9615101 | 5/1996 |
| WO | WO9617816 | 6/1996 |
| WO | WO9603318 | 10/1996 |
| WO | WO9633184 | 10/1996 |
| WO | WO9633187 | 10/1996 |
| WO | WO9636630 | 11/1996 |
| WO | WO 9641609 | 12/1996 |
| WO | WO 9731898 | 9/1997 |
| WO | WO 9736869 | 10/1997 |
| WO | WO 9813343 | 4/1998 |
| WO | 98/13355 | 4/1998 |
| WO | WO9820891 | 5/1998 |
| WO | WO9820892 | 5/1998 |
| WO | WO9820893 | 5/1998 |
| WO | WO 9822432 | 5/1998 |
| WO | WO9824805 | 6/1998 |
| ZA | 9207782 | 4/1993 |

OTHER PUBLICATIONS

Birkenshaw, T.N. et al., "Synthetic FKBP12 Ligands. Design and Synthesis of Pyranose Replacements," *Bioorganic & Medicinal Chemistry Letters*, (1994) 4:21, 2501–2506.

Caffrey, M.V. et al., "Synthesis and Evaluation of Dual Domain Macrocyclic FKBP12 Ligands," *Bioorganic & Medicinal Chemistry Letters*, (1994) 4:21, 2507–2510.

Hauske, J.R. et al. "Design and Synthesis of Novel FKBP Inhibitors," *J. of Medicinal Chemistry*, (1992) 35, 4284–4296.

Holt, D.A. et al., "Design, Synthesis, and Kinetic Evaluation of High–Affinity FKBP Ligands and the X–ray Crystal Structures of Their Complexes with FKBP12," *J. Am. Chem. Soc.*, (1993) 115, 9925–9938.

Holt, D.A. et al., "Structure–Activity Studies of Synthetic FKBP Ligands as Peptidyl–prolyl Isomers Inhibitors," *Bioorganic & Medicinal Chemistry Letters*, (1994) 4:2, 315–320.

Holt, D.A. et al., "Structure–Activity Studies of Nonmacrocyclic Rapamycin Derivatives," *Bioorganic & Medicinal Chemistry Letter*, (1993) 3:10, 1977–1980.

Luengo, J.I. et al, "Synthesis and Structure–Activity Relationships of Macrocyclic FKBP Ligands," *Bioorganic & Medicinal Chemistry Letters*, (1994) 4:2, 321–324.

Snyder, S.H. et al., "Immunophilins and the Nervous System," *Nature Medicine*, (1995) 1:1, 32–37.

Teague, S.J. et al., "Synthesis and Study of a Non–Macrocyclic FK506 Derivative," *Bioorganic & Medicinal Chemistry Letters*, (1994) 4:13, 1581–1584.

Steiner, et al., Chemical Abstract, vol. 126:272710, 1997.

Teague, S.J. et al., "The Affinity of the Excised Binding Domain of FK–506 for the Immunophilin FKBP12," *Bioorganic & Medicinal Chemistry Letters*, (1993) 3:10, 1947–1950.

Wang, G.T. et al., "Synthesis and FKBP Binding of Small Molecule Mimics of the Tricarbonyl Region of FK506," *Bioorganic and Medicinal Chemistry Letters*, (1994) 4:9, 1161–1166.

Yamashita, D.S. et al., "Design, Synthesis and Evaluation of Dual Domain FKBP Ligands," *Bioorganic & Medicinal Chemistry*, (1994) 4:2, 325–328.

Iwabuchi, T. et al., "Effects of immunosuppressive peptidyl–prolyl cis–trans isomerase (PPIase inhibitors, cyclosporin A, FK506, ascomycin and rapamycin, on hair growth initiation in mouse: immunosuppression is not required for hair growth," *J. of Dermatol. Sci.*, (1995) 9:1, 64–69.

Yamamoto, S. et al., "Stimulation of hair growth by topical application of FK506, a potent immunosuppressive agent," *J. Invest. Dermatol*, (1994) 102:2, 160–164.

Jiang, H. et al., "Induction of anagen in telogen mouse skin by topical application of FK506, a potent immunosuppressant," *J. Invest. Dermatol.*, (1995) 104:4, 523–525.

Askin, D. et al., "Effecient Degradation of FK–506 to a versatile synthetic intermediate," J. Org. Chem., 1990, 55 (20), 5451–4.

Goulet, Mark T., and Boger, Joshua, "Degradative studies on the tricarbonyl containing macrolide rapamycin," Tetrahedron Lett., 1990, 31(34), 4845–8.

Jones, T. et al., "Chemistry of tricarbonyl hemiketals and application of Evans technology to the total synthesis of the immunosuppressant (–)–FK–506," J. Am. Chem. Soc., 1990, 112(8), 2998–3017.

Jones, A. et al., "A formal synthesis of FK–506. Exploration of some alternatives to macrolactamization," J. Org. Chem., 1990, 55(9), 2786–97.

Rao, A.V., et al., "Studies directed towards the synthesis of immunosuppressive agent FK–506: construction of the tricarbonyl moiety," Tetrahedron Lett., 1990, 31(10), 1439–42.

Harding, M.W., et al., "A receptor for the immunosuppressant FK506 is a cis–trans peptidyl–prolyl isomerase," Nature Lett., 1989, 341, 758–60.

Finberg, Robert W. et al., "Prevention of HIV–1 Infection and Preservation of CD4 Function by the Binding of CPFs to gp120," Science, 1990, 249, 287–91.

Goodfellow, Val S. et al., "p–Nitrophenyl 3–diazopyruvate and diazopyruvamides, a New Family of Photoactivatable Cross–Linking Bioprobes," Biochemistry, 28(15), 6346–60.

Wasserman, H.H. et al., " Synthesis of the tricarbonyl region of FK–506 through and amidophosphorane [Erratum to document cited in CA111(7) :57366p]," J. Org. Chem., 1989, 54(22), 5406.

Wasserman, H.H. et al., "Synthesis of the tricarbonyl region of FK–506 through an amidosphere," J. Org. Chem., 1989, 54(12), 2785–6.

Askin, D. et al., "Chemistry of FK–506: benzilic acid rearrangement of the tricarbonyl system," Tetrahedron Lett., 1989, 30(6), 671–4.

Coleman, R., and Danishefsky, S., "Degradation and manipulations of the immunosuppressant FK506: preparation of potential synthetic intermediates," Heterocycles, 1989, 28(1), 157–61.

Boulmedais, Ali et al., "Stereochemistry of Electrochemical Reduction of Optically Active α–ketoamides. –II. Electroreduction of benzoylformamides derived from S–(–)–proline," Bull. Soc. Chim. Fr., 1989, (2), 185–91. (French).

Soai, Kenso et al., "Asymmetric Allylation of α–keto amides Derived from (S)–proline esters," Pept. Chem., 1986, 24, 327–330.

Egbertson, M. and Danishefsky, S., "A synthetic route to the tricarbonyl region of FK–506," J. Org. Chem., 1989, 54(1), 11–12.

Williams, D.R. and Benbow, J.W., "Synthesis of the α,β diketo amide segment of the novel immunosuppressive FK506," J. Org. Chem., 1988, 53(191), 4643–4.

Kocienski, P. et al., "A Synthesis of the C(1)–C(15) segment of tsukubaenolide (FK506)," Tetrahedron Lett., 1988, 29(35), 4481–4.

Tanaka, H. et al., "Structure of FK506, a novel imunosuppressant isolated from Streptomyces," J. Am. Chem. Soc., 1987, 109(16), 5031–3.

Soai, Kenso and Ishizaki, Miyuki, "Asymmetric Synthesis of Functionalized tertiary alcohols by diastereoselective allylation of chiral α–keto amides derived from (S)–proline esters: control of stereochemistry based on saturated coordination of Lewis acid," J. Org. Chem., 1986, 57(17) 3290–5. (English).

Soai, Kenso et al., "Asymmetric synthesis of both eaniomers of α–hydroxy acids by the diastereoselective reduction of chiral α–keto amides with complex metal hydrides in the presence of a metal salt," Chem. Lett., 1986, 11, 1897–900.

Soai, Kenso and Hasegawa, Hitoshi, "Diastereoselective reduction of chiral α–ketoamides derived from (S)–proline esters with sodium borohydride. Preparation of optically active α–hydroxy acids," J. Chem. Soc., 1985, 1(4), 769–72.

Soai, Kenso and Ishizaki, Miyuki, "Diastereoselective asymmetric allylation of chiral α–keto amides with allyltrimethylsilane. Preparation of protected homoallylic alcohols," J. Chem. Soc., 1984, 15, 1016–1017.

Bender, D., et al., "Periodate oxidation of α–keto γ–lactams. Enol oxidation and β–lactam formation. Mechanism of periodate hydroxylation reactions," J. Org. Chem., 1978, 43(17), 3354–62.

Colombo, L. et al., "Enantioselective synthesis of secondary alcohols in the presence of chiral ligands," Tetrahedron, 1982, 38(17), 2725–7.

Soai, Kenso et al., "Unusual effect of a mixed solvent on the asymmetric reduction of chiral α–keto amides with sodium borohydride," J. Chem. Soc., 1982, 21, 1282–3.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides," Synthesis, 1978, 8, 622–4. (German).

Cushman, D.W. et al., "Design of potent competitive inhibitors of angiotensin–converting enzyme. Carboxyalkanoyl and mercaptoalkanoyl amino acids," Biochemistry, 1977, 16(25), 5484–91.

Steglich, Wolfgang and Hinze, Sabine, "A rational synthesis of N–trifluroacetylamino acids," Synthesis, 1976, 8, 399–401. (German).

Marshall, J.A. et al., Convenient synthesis of dioxopiperazines via aminolysis of .alpha.–(pyruvylamino) esters, Synth. Commun., 1975, 5(3), 237–44.

Haeusler, Johannes and Schmidt, Ulrich, "Amino acids and peptides. IX. Pyruvoyl amino acids," Chem. Ber., 1974, 107(1), 145–51. (German).

Hearn, Walter R., and Worthington, Robert E., "L–Proline–N–oxalic anhydride," J. Org. Chem., 1967, 32(12), 4072–4.

Chakaraborty, Tushar K., "Studies towards the development of cyclic peptide–based analogs of macrolide immunosuppressants," Pure Appl. Chem., 1996, 68(3), 565–568.

Tugwell, Peter, "Clyclosporin in the Treatment of Rheumatoid Arthritis," J. of Autoimmunity, 1992, 5, 231–40.

Fry, Lionel, "Psoriasis: Immunopathology and Long–term treatment with Cyclosporin," J. of Autoimmunity, 1992, 5, 277–83.

Feutren, Gilles, "The Optimal use of Cyclosporin A in Autoimmune Diseases," J. of Autoimmunity, 1992, 5, 183–95.

Slee, Deborah H. et al., Selectivity in the Inhibition of HIV and FIV Protease: Inhibitory and Mechanistic Studies of Pyrrolidine–Containing α–Keto Amide and Hydroxyethylamine Core Structures, J. Am. Chem. Soc., 1995, 117(48), 1187–78.

Nicolaou, K.C. et al., "Total synthesis of rapamycin," Che.—Eur. J., 1995, 1(5), 318–33.

Munoz, Benito et al., "α–Ketoamide Phe–Pro isostere as a new core structure for the inhibition of HIV protease," Bioorg. Med. Chem., 1994, 2(10), 1085–90.

Hauske, James R. et al., "Investigation of the effects of synthetic, non–cytotoxic immunophilin inhibitors on MDR," Bioorg. Med. Chem.. Lett., 1994, 4(17), 2097–102.

Mashkovskii, M.D. et al., "1–[4–(2–Hydroxy–3–tert–butylaminopropoxy)–indole–3–yl (5–acetamido–1–(S)–carboxypentyl)–DL–alanyl]–L–proline dihydrochloride, a new angiotensin–converting enzyme inhibitor with β–adrenoblocking properties," Khim.–Farm. Zh., 1993, 27(10), 16–20. (Russian).

Ranganathan, Darshan et al., "Protein Backbone Modification by Novel Cα–C Side–Chain Scission," 1994, J. Am. Chem. Soc., 116(15), 6545–57.

Baader, Ekkehard et al., "Inhibition of prolyl 4–hydroxylase by oxalyl amino acid derivatives in vitro, in isolated microsomes and in embryonic chicken tissues," Biochem. J., 1994, 300(2), 525–30.

Gold, Bruce R., et al., "The Immunosuppressant FK506 Increases the Rate of Axonal Regeneration in Rat Sciatic Nerve," J. Neuroscience, 1995, 15(11):7509–7516.

Karle, Isabella L. et al., "Coformation of the oxalamide group in retro–bispeptides. Three crystal structures," Int. J. Pept. Protein Res., 1994, 43(2), 160–5.

Kaczmar, et al., Makromol. Chem., 1976, 177, 1981–9 (German).

Steiner, Joseph P. et al., "High brain densities of the immunophilin FKBP colocalized with calcineurin," Nature Lett., 1992, 358, 584–7.

Pattenden, Gerald and Tankard, Mark, "Facile Synthesis of the tricarbonyl subunit in the immunosuppressant rapamycin," Tetrahedron Lett., 1993, 34(16), 2677–80.

Furber, M. et al., "Studies relating to the immunosuppressive activitiy of FK506," Tetrahedron Lett., 1993, 34(8), 1351–4.

Ranganathan, Darshan et al., "Oxalopeptides as core motifs for protein design," J. Chem. Soc., 1993, (1), 92–4.

Dawson, Ted M. et al., "Immunosuppressant FK506 enhances phosphorylation of nitric oxide synthase and protects against flutamate neurotoxicity," Proc. Natl. Acad. Sci. USA, 1993, 90, 9808–12.

Cunliffe, C. Jane et al., "Novel inhibitors of prolyl 4–hydroxylase. 3. Inhibition by the substrate analog N–oxaloglycine and its derivatives," J. Med. Chem., 1992, 35 (14), 2652–8.

Waldmann, Herbert, "Amino acid esters as chiral auxiliaries in Barbier–type reactions in aqueous solutions," Liebigs Ann. Chem., 1991, (12), 1317–22. (German).

Krit, N.A. et al., "Impact of the nature of alkyl radical on the biological activity of N–carboxyalkyl dipeptides," Khim.–Farm. Zh., 1991, 25(7), 44–6. (Russian).

Blaschke et al., Chemical Abstracts, 1974, 85:78405k.

Caufield, Craig E. and Musser, John H., "Macrocyclic Immunomodulators," *Annual Reports in Medicinal Chemistry*, Johns (Ed.), Academic Press, Chapter 21, 195–204, 1989.

Effenberger F. et al., "Diastereoselective addition of benzenesulfenyl chloride to 1–acryloylproline esters," Chemical Abstracts, 1989, 110:154846h.

Nakatsuka, M et al., " Total Synthesis of FK506 and an FKBP Reagent, ($C_8$, $C_9$– $^{13}$ $C_2$)–FK–506," J. Am. Chem. Soc., 1990, 112 (14), 5583–90.

Shu, A. et al., "Synthesis of I–125 labeled photoaffinity rapamycin analogs," J. Labelled Compd. Radiopharm., 1996, 38(3), 277–37.

Tatlock, J. et al., "High affinity FKBP–12 ligands from (R)–(–)–carvone. Synthesis and evaluation of FK506 pyranose ring replacements," Bioorg. Med. Chem. Lett., 1995, 5(21), 2489–94.

Teague, S. et al., "Synthesis of FK506–cyclosporin hybrid macrocycles," Bioorg. Med. Chem. Lett., 1995, 5(20), 2341–6.

Stocks, M. et al., "Macrocyclic ring closures employing the intramolecular Heck reaction," Tetrahedron Lett., 1995, 36(36), 6555–8.

Wang, C.P. et al., "High performance liquid chromatographic isolation and spectroscopic characterization of three major metabolites from the plasma of rats receiving rapamycin (sirolimus) orally," J. Liq. Chromatogr., 1995, 18(13), 2559–68.

Armistead, D.M. et al., "Design, synthesis and structure of non–macrocyclic inhibitors of FKBP12, the major binding protin for the immunosuppressant FK506," Acta Crystallogr. 1995, D51(4), 522–8.

Luengo, J. et al., "Structure–activity studies of rapamycin analogs: evidence that the C–7 methodoxy group is part of the effector domain and positioned at the FKBP:12–FRAP interface," Chem. Biol., 1995, 2(7), 471–81.

Furber, Mark, "FKBP–12–ligand–calceineurin interactions: analogs of SBL506," J. Am. Chem. Soc., 1995, 117(27), 7267–8.

Chakraborty, TK et al., "Design and Synthesis of a rapamycin–based high affinity binding FKBP12 ligand," Chem. Biol., 1995, 2(3), 157–61.

Wang, C.P. et al., "A high performance liquid chromatographic method for the determination of rapamycin {sirolimus} in rat serum, plasma, and blood and in monkey serum," J. Liq. Chromatogr., 1995, 18(9), 1801–8.

Smith, A.B. et al., "Total synthesis of rapamycin and demethoxyrapamycin," J. Am. Chem. Soc., 1995, 117(19).

Baumann, K. et al., "Synthesis and oxidative cleavage of the major equilibrium products of ascomycin and Fk 506," Tetrahedron Lett., 1995, 26(13), 2231–4.

Nelson, F. et al., "A novel ring contraction of rapamycin," Tetrahedron Lett., 1994, 35(41), 7557–60.

Dawson, T.M. et al., "The immunophilins, FK506 binding and cyclophilin, are discretely localized in the brain: relationship to calcineurin," Neuroscience, 1994, 62(2), 569–80.

Cameron, Andrew et al., "Immunophilin FK506 binding protein associated with inositol 1,4,5–triphosphate receptor modulates calcium flux," Proc. Natl. Acad. Sci. USA, 1995, 92, 1784–1788.

Stocks, M. et al., "The contribution to the binding of the pyranoside sustituents in the excised binding domain of FK–506," Bioorg. Med. Chem. Lett., 1994, 4(12), 1457–60.

Steiner, J.P. et al., "Nonimmunosuppressive Ligands for Neuroimmunophilins Promote Nerve Extension In Vitro and In Vivo," Society for Neuroscience Abstracts, 1996, 22, 297.13.

Lyons, W. Ernest et al., "Neronal Regeneration Enhances the Expression of the Immunophilin FKBP–12," The Journal of Neuroscience, 1995, 15, 2985–94.

Skotnicki, Jerauld et al., "Ring expanded rapamycin derivatives," Tetrahedron Lett., 1994, 35(2), 201–2.

Skotnicki, Jerauld et al., "Synthesis of secorapamycin esters and amides," Tetrah. Lett., 1994, 35(2), 197–200.

Rao, A.V. Rama and Desibhatla, Vidyanand, "Studies directed towards the synthesis of rapamycin: stereoselective synthesis of C–1 to C–15 segment," Tetrahedron Lett., 1993, 34(44), 7111–14.

Andrus, Merrit B., "Structure–based design of an acyclic ligand that bridges FKBP12 and calcineurin," J. Am. Chem. Soc., 1993, 115(2), 10420–1.

Luengo, Juan I. et al., "Efficient removal of pipecolinate from rapamycin and FK506 by reaction with tetrabutylammonium cyanide," Tetrahedron Lett., 1993, 34(29), 4599–602.

Steffan, Robert J. et al., "Base catalyzed degradations of rapamycin," Tetrahedron Lett., 1993, 34(23), 3699–702.

Nicolaou, K.C. et al., "Total Synthesis of rapamycin," J. Am. Chem. Soc., 1993, 115(10), 4419–20.

Hayward, C.M. et al., "Total Synthesis of rapamycin via a novel titanium–mediated aldol macrocyclization reaction," J. Am. Chem. Soc., 1993, 115(20), 9345–6.

Yohannes, Daniel et al., "Degradation of rapamycin: synthesis of a rapamycin–derived fragment containing the tricarbonyl and triene sectors,"Tetrahedron Lett., 1993, 34(13), 2075–8.

Luengo, J. et al., "Studies on the chemistry of rapamycin: novel transformation under Lewis–acid catalysis," Tetrahedron Lett., 1993, 34(6), 991–4.

Yohannes, Daniel et al., "Degradation of rapamycin: retrieval of major intact subunits," Tetrahedron Lett., 1992, 33(49), 7469–72.

Goulet, Mark T. and Boger, Joshua, "Degradative studies on the tricarbonyl containing macrolide rapamycin," Tetrahedron Lett., 1991, 32(45), 6454.

Goulet, Mark T. et al., "Construction of the FK–506 analog from rapamycin–derived materials," Tetrahedron Lett., 1991, 32(36), 4627–30.

Rao, A.V. Rama et al., "Studies directed towards the synthesis of immunosuppressive agent FK–506: synthesis of the entire bottom half," Tetrahedron Lett., 1991, 32(9), 1251–4.

Fisher, Matthew et al., "On the remarkable propensity for carbon–carbon bond cleavage reactions in teh C(8) –C(10) region of FK–506," J. Org. Chem., 1991, 56(8), 2900–7.

Linde, Robert G. et al., "Straightforward synthesis of 1,2,3–tricarbonyl systems," J. Org. Chem., 1991, 56(7), 2534–8.

Hayward, C.M. et al., "An application of the Suarez reaction to the regiospecific synthesis of the $C_{29}$–$C_{42}$ segment of rapamycin," 3989–92.

Hovarth, R., et al., "An application of the Evans–Prasad 1,3–Syn diol synthesis to a stereospecific synthesis of the $C_{10}$–$C_{27}$ segment of rapamycin," Tetrahedron Lett., 1993, 34(25), 3993–3996.

Whitesell, J.K. et al., "Asymmetric Induction. Reduction, Nucleophilic Addition to, Ene Reactions of Chiral α–Ketoesters," J. Chem. Soc., Chem Commun., 1983, 802.

Ando, Takao et al., "Formation of Crossed Phenzine from the Reaction between Tetra–p–anisyl– and Tetra–p–tolylhydrazines in Liquid Sulphur Dioxide," Chem. Comm., S. Chem. Comm., 1975, 989.

Kino, Toru et al., "FK506, A novel immunosuppressnt isolateded from A streptomyces," J. of Antibiotics, 1987, 40(9), 1249–55.

Waldmann, Herbert, "Proline benzyl ester as chiral auxilary in Barbier–type reactions in aqueous solution," 1990, Synlett, 19, 627–8.

Steiner, Joseph P., et al., "Neurotrophic Immunophilin Liagnds Stimulate Structural and Functional Recovery in Neurodegenerative Animal Models," 1997, Proc. Natl. Aced. Sci. USA, 94:2019–2024.

Steiner, Joseph P., et al., "Neurotrophic Actions of Nonimmunosuppressive Analogues of Immunosuppressive Drugs FK506, Rapamycin and Cyclosporin A," Nat. Med. 3(4) :421–428.

Maurer, Marcus, et al., *Hair Growth Modulation by Topical Immunophilin Ligands*, Am. J. Path. 150:1433–41 (1997).

CA 138:270602, WO 98/13355, Li et al. (Apr. 2, 1998).

\* cited by examiner

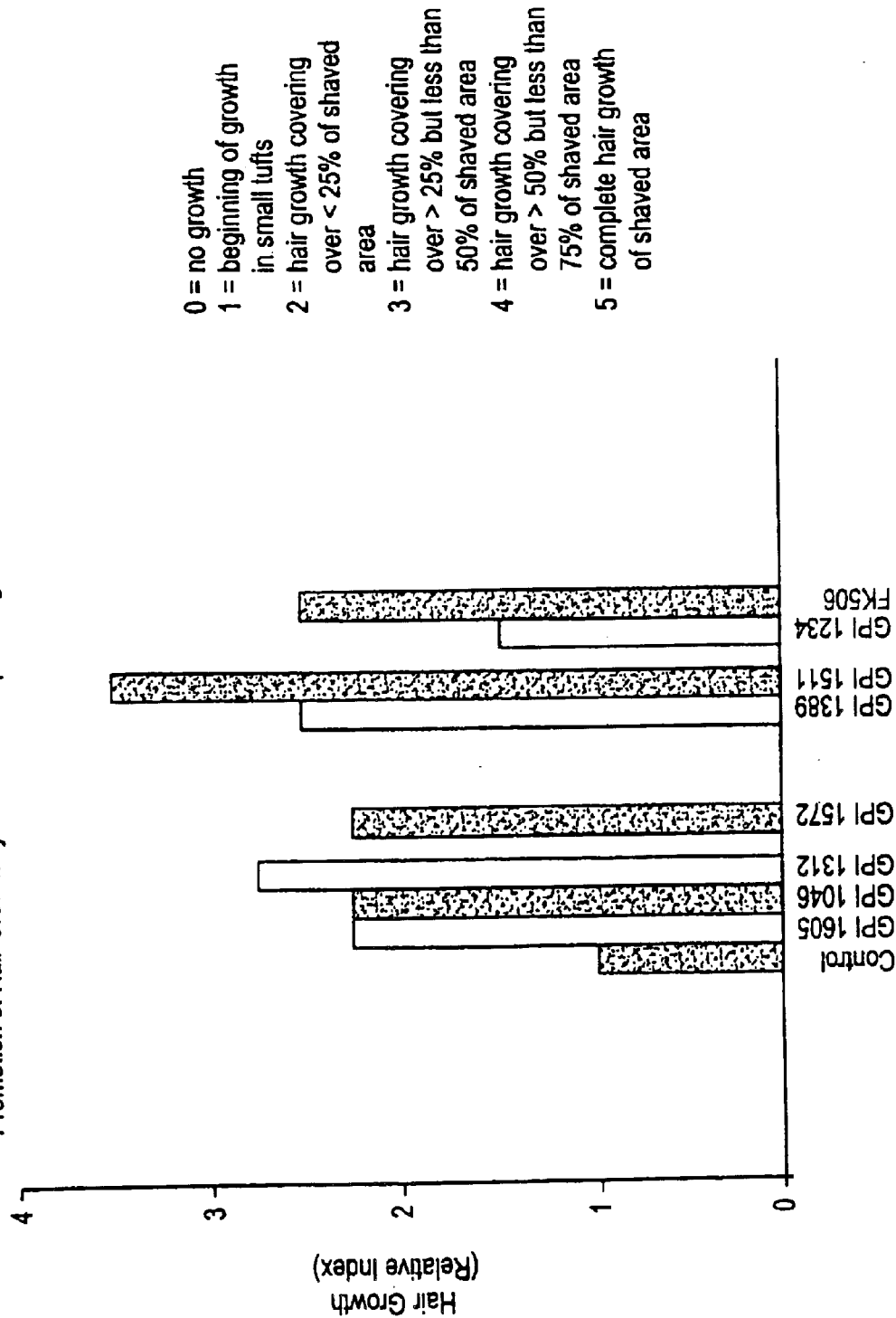

PYRROLIDINE DERIVATIVE HAIR GROWTH COMPOSITIONS AND USES

This application is a continuation of application Ser. No. 09/893,567, filed on Jun. 29, 2001, now abandoned which is a continuation-in-part of U.S. patent application Ser. No. 09/089,416, filed on Jun. 3, 1998, now abandoned, which is a continuation-in-part of U.S. patent application Ser. No. 08/869,426, filed on Jun. 4, 1997, now U.S. Pat. No. 5,945,441, the entire contents of which are herein incorporated by reference.

BACKGROUND OF THE INVENTION

1. Field of Invention

This invention relates to pharmaceutical compositions methods for treating alopecia and promoting hair growth using pyrrolidine derivatives.

2. Description of Related Art

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., J. Invest. Dermatol., 1994, 102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for non-immunosuppressant, small molecule compounds which are useful as hair revitalizing compounds.

Hamilton and Steiner disclose in U.S. Pat. No. 5,614,547 novel pyrrolidine carboxylate compounds which bind to the immunophilin FKBP12 and stimulate nerve growth, but which lack immunosuppressive effects. Unexpectedly, it has been discovered that these non-immunosuppressant compounds promote hair growth with an efficacy similar to FK506. Yet their novel small molecule structure and non-immunosuppressive properties differentiate them from FK506 and related immunosuppressive compounds found in the prior art.

SUMMARY OF THE INVENTION

The present invention relates to a method for treating alopecia or promoting hair growth in an animal in need thereof, which comprises administering to said animal an effective amount of a pyrrolidine derivative.

The present invention further relates to a pharmaceutical composition which comprises:

(i) an effective amount of a pyrrolidine derivative for treating alopecia or promoting hair growth in an animal in need thereof; and (ii) a pharmaceutically acceptable carrier.

The pyrrolidine derivative used in the inventive method and pharmaceutical composition preferably has an affinity for FKBP-type immunophilins and does not exert any significant immunosuppressive activity.

BRIEF DESCRIPTION OF THE DRAWINGS

FIG. 1 shows the condition of the mice prior to the experiment.

FIG. 2 shows that less than 3% of the shaved area is covered with new hair growth when tale vehicle (control) is administered.

FIG. 3 shows the remarkable effects of pyrrolidine derivatives wherein 90% of the shaved area is covered with new hair growth.

FIG. 4 shows the remarkable ability of pyrrolidine derivatives to achieve, essentially, complete hair regrowth in the shaved area.

FIG. 5 is a bar graph depicting the relative hair growth indices of mice treated with a vehicle, FK506, pyrrolidine derivatives of the present invention, and various related compounds 14 days after treatment with each identified compound. FIG. 5 demonstrates the remarkable early hair growth promoted by pyrrolidine derivatives and other related compounds.

DETAILED DESCRIPTION OF THE INVENTION

Definitions

Figure 1:
FIG. 1 is a photograph of C57 Black 6 mice before being shaved for the experiment.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"GPI 1605" refers to a compound of formula

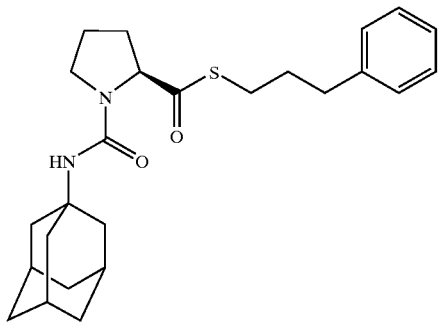

GPI 1605

"GPI 1046" refers to 3-(3-pyridyl)-1-propyl (2s)-1-(3,3-dimethyl-1,2-dioxopentyl)-2-pyrrolidinecarboxylate, a compound of formula

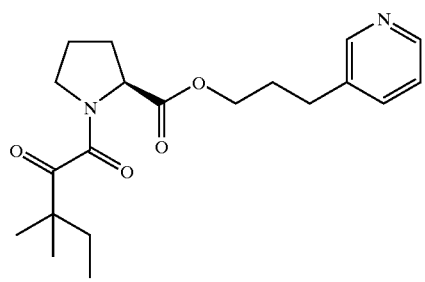

GPI1046

"GPI 1312" refers to a compound of formula

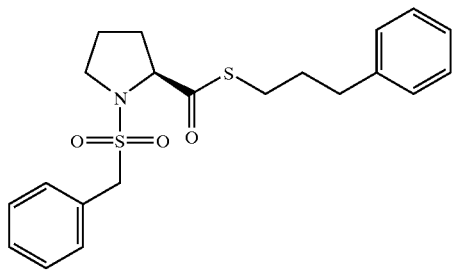

GPI 1312

"GPI 1572" refers to a compound of formula

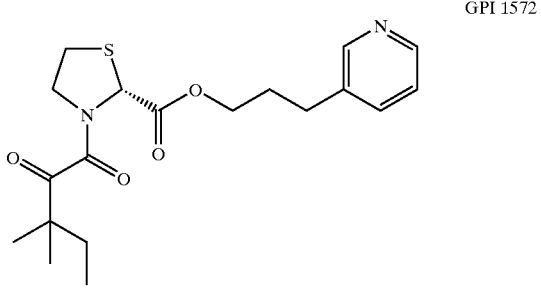

GPI 1572

"GPI 1389" refers to a compound of formula

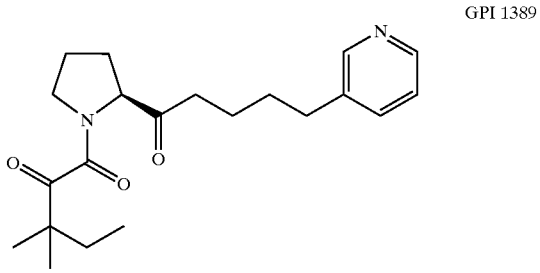

GPI 1389

"GPI 1511" refers to a compound of formula

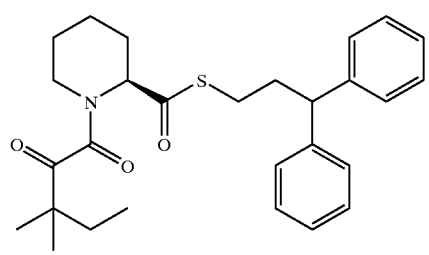

GPI 151

"GPI 1234" refers to a compound of formula

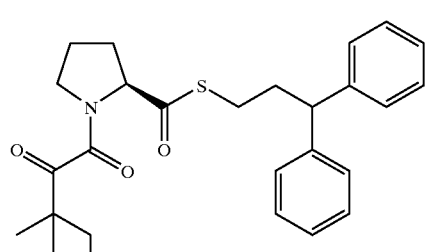

GPI 123

"Isomers" refer to different compounds that have the same molecular formula. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

"Pharmaceutically acceptable salt" refers to a salt of the inventive compounds which possesses the desired pharmacological activity and which is neither biologically nor otherwise undesirable. The salt can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Examples of a base salt include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. Also, the basic nitrogen-containing groups can be quarternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Pilar cycle" refers to the life cycle of hair follicles, and includes three phases:

(1) the anagen phase, the period of active hair growth which, insofar as scalp hair is concerned, lasts about three to five years;
(2) the catagen phase, the period when growth stops and the follicle atrophies which, insofar as scalp hair is concerned, lasts about one to two weeks; and
(3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:
(i) preventing alopecia in an animal which may be predisposed to alopecia; and/or
(ii) inhibiting, retarding or reducing alopecia; and/or
(iii) promoting hair growth; and/or
(iv) prolonging the anagen phase of the hair cycle; and/or
(v) converting vellus hair to growth as terminal hair.

Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

Methods of the Present Invention

The present invention relates to a method for treating alopecia or promoting hair growth in an animal, which comprises administering to said animal an effective amount of a pyrrolidine derivative.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

Pharmaceutical Compositions of the Present Invention

The present invention also relates to a pharmaceutical composition comprising:
(i) an effective amount of a pyrrolidine derivative for treating alopecia or promoting hair growth in an animal in need thereof; and
(ii) a pharmaceutically acceptable carrier.

Pyrrolidine Derivatives

The pyrrolidine derivative used in the method and pharmaceutical composition of the present invention is preferably a low molecular weight, small molecule compound having an affinity for an FKBP-type immunophilin, such as FKBP12. When the compound binds to an FKBP-type immunophilin, it has been found to inhibit the prolyl-peptidyl cis-trans isomerase activity, or rotamase, activity of the binding protein. Unexpectedly, the compound has also been found to stimulate hair growth. Preferably, the compound is devoid of any significant immunosuppressive activity.

Examples of a pyrrolidine derivative that may be used in the inventive method and pharmaceutical composition are set forth below.

Formula I

A compound of the invention may be of formula I

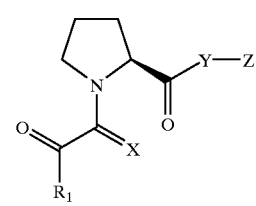

or a pharmaceutically acceptable salt, ester, or solvate thereof, wherein:

$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

X is O, S, $CH_2$, or two hydrogen atoms;
Y is O or $NR_2$;
$R_2$ is hydrogen or $C_1$–$C_6$ alkyl;
Z is $C_1$–$C_6$ straight or branched chain alkyl, or $C_2$–$C_6$ straight or branched chain alkenyl,
wherein said Z is substituted with one or more substituent(s) independently selected from the group consisting of $Ar_1$, $C_3$–$C_8$ cycloalkyl, $C_1$–$C_6$ straight or branched chain alkyl substituted with $C_2$–$C_8$ cycloalkyl, and $C_2$–$C_6$ straight or branched chain alkenyl substituted with $C_3$–$C_8$ cycloalkyl,
or Z is the fragment

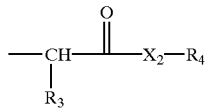

wherein:
$R_3$ is $C_1$–$C_9$ straight or branched chain alkyl which is unsubstituted or substituted with $C_3$–$C_8$ cycloalkyl or $Ar_1$;
$X_2$ is O or $NR_5$;
$R_5$ is selected from the group consisting of hydrogen, $C_1$–$C_6$ straight or branched chain alkyl, and $C_2$–$C_6$ straight or branched chain alkenyl; and
$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

In a preferred embodiment of formula I, Z and $R_1$ are lipophilic.

In a more preferred embodiment of formula I, the compound is selected from the group consisting of:
3-phenyl-1-propyl (2S)-1-(3,3-dimethyl-1,2-dioxopentyl)-2-pyrrolidinecarboxylate;
3-phenyl-1-prop-2-(E)-enyl (2S)-1-(3,3-dimethyl-1,2-dioxopentyl)-2-pyrrolidinecarboxylate;
3-(3,4,5-trimethoxyphenyl)-1-propyl (2S)-1-(3,3-dimethyl-1,2-dioxopentyl)-2-pyrrolidinecarboxylate;
3-(3,4,5-trimethoxyphenyl)-1-prop-2-(E)-enyl (2S)-1-(3,3-dimethyl-1,2-dioxopentyl)-2-pyrrolidinecarboxylate;
3-(4,5-dichlorophenyl)-1-propyl (2S)-1-( 3,3-dimethyl-1,2-dioxopentyl)-2-pyrrolidinecarboxylate;
3-(4,5-dichlorophenyl)-1-prop-2-(E)-enyl (2S)-1-(3,3-dimethyl-1,2-dioxopentyl)-2-pyrrolidinecarboxylate;
3-(4,5-methylenedioxyphenyl)-1-propyl (2S)-1-(3,3-dimethyl-1,2-dioxopentyl)-2-pyrrolidinecarboxylate;
3-(4,5-methylenedioxyphenyl)-1-prop-2-(E)-enyl (2S)-1-(3,3-dimethyl-1,2-dioxopentyl)-2-pyrrolidinecarboxylate;
3-cyclohexyl-1-propyl (2S)-1-(3,3-dimethyl-1,2-dioxopentyl)-2-pyrrolidinecarboxylate;
3-cyclohexyl-1-prop-2-(E)-enyl (2S)-1-(3,3-dimethyl-1,2-dioxopentyl)-2-pyrrolidinecarboxylate;
(1R)-1,3-diphenyl-1-propyl (2S)-1-(3,3-dimethyl-1,2-dioxopentyl)-2-pyrrolidinecarboxylate;
(1R)-1,3-diphenyl-1-prop-2-(E)-enyl (2S)-1-(3,3-dimethyl-1,2-dioxopentyl)-2-pyrrolidinecarboxylate;
(1R)-1-cyclohexyl-3-phenyl-1-propyl (2S)-1-(3,3-dimethyl-1,2-dioxopentyl)-2-pyrrolidinecarboxylate;
(1R)-1-cyclohexyl-3-phenyl-1-prop-2-(E)-enyl (2S)-1-(3,3-dimethyl-1,2-dioxopentyl)-2-pyrrolidinecarboxylate;
(1R)-1-(4,5-dichlorophenyl)-3-phenyl-1-propyl (2S)-1-(3,3-dimethyl-1,2-dioxopentyl)-2-pyrrolidinecarboxylate;
3-phenyl-1-propyl (2S)-1-(1,2-dioxo-2-cyclohexyl)ethyl-2-pyrrolidinecarboxylate;

3-phenyl-1-propyl (2S)-1-(1,2-dioxo-4-cyclohexyl)butyl-2-pyrrolidinecarboxylate;
3-phenyl-1-propyl (2S)-1-(1,2-dioxo-2-[2-furanyl])ethyl-2-pyrrolidinecarboxylate;
3-phenyl-1-propyl (2S)-1-(1,2-dioxo-2-[2-thienyl])ethyl-2-pyrrolidinecarboxylate;
3-phenyl-1-propyl (2S)-1-(1,2-dioxo-2-[2-thiazolyl])ethyl-2-pyrrolidinecarboxylate;
3-phenyl-1-propyl (2S)-1-(1,2-dioxo-2-phenyl)ethyl-2-pyrrolidinecarboxylate;
1,7-diphenyl-4-heptyl (2S)-1-(3,3-dimethyl-1,2-dioxopentyl)-2-pyrrolidinecarboxylate;
3-phenyl-1-propyl (2S)-1-(3,3-dimethyl-1,2-dioxo-4-hydroxybutyl)-2-pyrrolidinecarboxylate;
3-phenyl-1-propyl (2S)-1-(3,3-dimethyl-1,2-dioxopentyl)-2-pyrrolidinecarboxamide;
1-[1-(3,3-dimethyl-1,2-dioxopentyl)-L-proline]-L-phenylalanine ethyl ester;
1-[1-(3,3-dimethyl-1,2-dioxopentyl)-L-proline]-L-leucine ethyl ester;
1-[1-(3,3-dimethyl-1,2-dioxopentyl)-L-proline]-L-phenylglycine ethyl ester;
1-[1-(3,3-dimethyl-1,2-dioxopentyl)-L-proline]-L-phenylalanine phenyl ester;
1-[1-(3,3-dimethyl-1,2-dioxopentyl)-L-proline]-L-phenylalanine benzyl ester; and
1-[1-(3,3-dimethyl-1,2-dioxopentyl)-L-proline]-L-isoleucine ethyl ester;
or a pharmaceutically acceptable salt, ester, or solvate thereof.

Formula II

Additionally, a compound of the invention may be of formula II

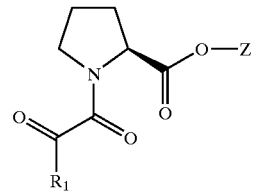

or a pharmaceutically acceptable salt, ester, or solvate thereof, wherein:
$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$,
wherein said $R_1$ is unsubstituted or substituted with one or more substituents independently selected from the group consisting of $C_1$–$C_6$ alkyl, $C_2$–$C_6$ alkenyl, $C_3$-$C_8$ cycloalkyl, $C_5$–$C_7$ cycloalkenyl, hydroxy, and $Ar_2$;
$Ar_1$ and $Ar_2$ are independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl,
wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;
Z is $C_1$–$C_6$ straight or branched chain alkyl, or $C_2$-C6 straight or branched chain alkenyl, wherein said Z is substituted with one or more substituent(s) independently selected from the group consisting of $Ar_1$, $C_3$–$C_8$ cycloalkyl, $C_1$–$C_6$ straight or branched chain alkyl substituted with $C_3$–$C_8$ cycloalkyl, and $C_2$–$C_6$ straight or branched chain alkenyl substituted with $C_3$–$C_8$ cycloalkyl, or Z is the fragment

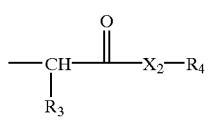

wherein:
$R_3$ is $C_1$–$C_9$ straight or branched chain alkyl which is unsubstituted or substituted with $C_3$–$C_8$ cycloalkyl or $Ar_1$;
$X_2$ is O or $NR_5$;
$R_5$ is selected from the group consisting of hydrogen, $C_1$–$C_6$ straight or branched chain alkyl, and $C_2$–$C_6$ straight or branched chain alkenyl; and
$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

In a preferred embodiment of formula II, $R_1$ is selected from the group consisting of $C_1$–$C_9$ straight or branched chain alkyl, 2-cyclohexyl, 4-cyclohexyl, 2-furanyl, 2-thienyl, 2-thiazolyl, and 4-hydroxybutyl.

In another preferred embodiment of formula II, Z and $R_1$ are lipophilic.

Formula III

Furthermore, a compound of the invention may be of formula III

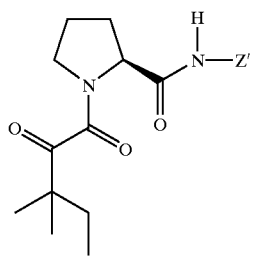

III or a pharmaceutically acceptable salt, ester, or solvate or hydrate thereof, wherein:
Z' is the fragment

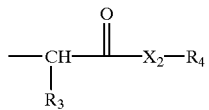

wherein:
$R_3$ is $C_1$–$C_9$ straight or branched chain alkyl or unsubstituted $Ar_1$,
wherein said alkyl is unsubstituted or substituted with $C_3$–$C_8$ cycloalkyl or $Ar_1$;
$X_2$ is O or $NR_5$;
$R_5$ is selected from the group consisting of hydrogen, $C_1$–$C_6$ straight or branched chain alkyl, and $C_2$–$C_6$ straight or branched chain alkenyl;

$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl; and $Ar_1$ is independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl,
wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino.

In a preferred embodiment of formula III, Z' is lipophilic.

Formula IV

A compound of the invention may also be of formula IV

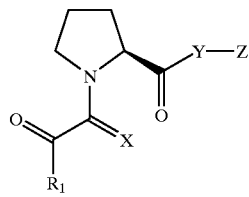

IV or a pharmaceutically acceptable salt, ester, or solvate thereof, wherein:
$R_1$ is $C_1$–$C_6$ straight or branched chain alkyl, $C_2$–$C_6$ straight or branched chain alkenyl, $C_3$–$C_6$ cycloalkyl or $Ar_1$,
wherein said alkyl or alkenyl is unsubstituted or substituted with $C_3$–$C_6$ cycloalkyl or $Ar_2$;
$Ar_1$ and $Ar_2$ are independently selected from the group consisting of 2-furyl, 2-thienyl, and phenyl;
X is selected from the group consisting of oxygen and sulfur;
Y is oxygen;
Z is $C_1$–$C_6$ straight or branched chain alkyl or $C_2$–$C_6$ straight or branched chain alkenyl,
wherein said Z is substituted with one or more substituent(s) independently selected from the group consisting of 2-furyl, 2-thienyl, $C_3$–$C_6$ cycloalkyl, pyridyl, and phenyl, each having one or more substituent(s) independently selected from the group consisting of hydrogen and $C_1$–$C_4$ alkoxy.

In a preferred embodiment of formula IV, Z and $R_1$ are lipophilic.

In another preferred embodiment of formula IV, the compound is selected from the group consisting of:
3-(2,5-dimethoxyphenyl)-1-propyl (2S)-1-(3,3-dimethyl-1,2-dioxopentyl)-2-pyrrolidinecarboxylate;
3-(2,5-dimethoxyphenyl)-1-prop-2-(E)-enyl (2S)-1-(3,3-dimethyl-1,2-dioxopentyl)-2-pyrrolidinecarboxylate;
2-(3,4,5-trimethoxyphenyl)-1-ethyl (2S)-1-(3,3-dimethyl-1,2-dioxopentyl)-2-pyrrolidinecarboxylate;
3-(3-pyridyl)-1-propyl (2S)-1-(3,3-dimethyl-1,2-dioxopentyl)-2-pyrrolidinecarboxylate;
3-(2-pyridyl)-1-propyl (2S)-1-(3,3-dimethyl-1,2-dioxopentyl)-2-pyrrolidinecarboxylate;
3-(4-pyridyl)-1-propyl (2S)-1-(3,3-dimethyl-1,2-dioxopentyl)-2-pyrrolidinecarboxylate;

3-phenyl-1-propyl (2S)-1-(2-tert-butyl-1,2-dioxoethyl)-2-pyrrolidinecarboxylate;

3-phenyl-1-propyl (2S)-1-(2-cyclohexylethyl-1,2-dioxoethyl)-2-pyrrolidinecarboxylate;

3-(3-pyridyl)-1-propyl (-2S)-1-(2-cyclohexylethyl-1,2-dioxoethyl)-2-pyrrolidinecarboxylate;

3-(3-pyridyl)-1-propyl (2S)-1-(2-tert-butyl-1,2-dioxoethyl)-2-pyrrolidinecarboxylate;

3,3-diphenyl-1-propyl (2S)-1-(3,3-dimethyl-1,2-dioxopentyl)-2-pyrrolidinecarboxylate;

3-(3-pyridyl)-1-propyl (2S)-1-(2-cyclohexyl-1,2-dioxoethyl)-2-pyrrolidinecarboxylate;

3-(3-pyridyl)-1-propyl (2S)-N-([2-thienyl]glyoxyl)pyrrolidinecarboxylate;

3,3-diphenyl-1-propyl (2S)-1-(3,3-dimethyl-1,2-dioxobutyl)-2-pyrrolidinecarboxylate;

3,3-diphenyl-1-propyl (2S)-1-cyclohexylglyoxyl-2-pyrrolidinecarboxylate; and 3,3-diphenyl-1-propyl (2S)-1-(2-thienyl)glyoxyl-2-pyrrolidinecarboxylate;

or a pharmaceutically acceptable salt, ester, or solvate thereof.

In a more preferred embodiment of formula IV, the compound is selected from the group consisting of:

3-(3-pyridyl)-1-propyl (2S)-1-(3,3-dimethyl-1,2-dioxopentyl)-2-pyrrolidinecarboxylate;

3-(2-pyridyl)-1-propyl (2S)-1-(3,3-dimethyl-1,2-dioxopentyl)-2-pyrrolidinecarboxylate; and 3-(3-pyridyl)-1-propyl (2S)-1-(2-cyclohexyl-1,2-dioxoethyl)-2-pyrrolidinecarboxylate;

or a pharmaceutically acceptable salt, ester, or solvate thereof.

In the most preferred embodiment of formula IV, the compound is 3-(3-pyridyl)-1-propyl (2S)-1-(3,3-dimethyl-1,2-dioxopentyl)-2-pyrrolidine-carboxylate, and pharmaceutically acceptable salts, esters, and solvates thereof.

Formula V

Additionally, a compound of the invention may be of formula V

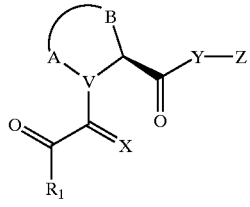

V or a pharmaceutically acceptable salt, ester, or solvate thereof, wherein:

V is CH or N;

A and B, taken together with V and the carbon atom to which they are respectively attached, form a 5–7 membered saturated or unsaturated heterocyclic ring containing one or more heteroatom(s) selected from the group consisting of O, S, SO, $SO_2$, N, NH, and NR;

R is $C_1$–$C_9$ straight or branched chain alkyl, $C_2$–$C_9$ straight or branched chain alkenyl, $C_3$–$C_9$ cycloalkyl, $C_5$–$C_7$ cycloalkenyl, or $Ar_1$, wherein said R is either unsubstituted of substituted with one or more substituent(s) independently selected from the group consisting of halo, haloalkyl, carbonyl, carboxy, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, thioalkyl, alkylthio, sulfhydryl, amino, alkylamino, aminoalkyl, aminocarboxyl, and $Ar_2$;

$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_1$, wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently an alicyclic or aromatic, mono-, bi- or tricyclic, carbo- or heterocyclic ring, wherein the ring is either unsubstituted or substituted with one or more substituent(s), wherein the individual ring size is 5–8 members, wherein said heterocyclic ring contains 1–6 heteroatom(s) independently selected from the group consisting of O, N, and S;

X is O, S, $CH_2$, or two hydrogen atoms;

Y is O or $NR_2$;

$R_2$ is hydrogen or $C_1$–$C_6$ alkyl;

Z is $C_1$–$C_6$ straight or branched chain alkyl or $C_2$–$C_6$ straight or branched chain alkenyl, wherein said Z is substituted with one or more substituent(s) independently selected from the group consisting of $Ar_1$, $C_3$–$C_8$ cycloalkyl, $C_1$–$C_6$ straight or branched chain alkyl substituted with $C_3$–$C_8$ cycloalkyl, and $C_2$–$C_6$ straight or branched chain alkenyl, or Z is the fragment

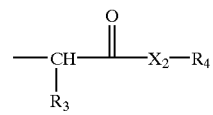

wherein:

$R_3$ is $C_1$–$C_9$ straight or branched chain alkyl which is unsubstituted or substituted with $C_3$–$C_8$ cycloalkyl or $Ar_1$;

$X_2$ is O or $NR_5$;

$R_5$ is selected from the group consisting of hydrogen, $C_1$–$C_6$ straight or branched chain alkyl, and $C_2$–$C_6$ straight or branched chain alkenyl; and $R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl.

All the compounds of Formulas I–V possess asymmetric centers and thus can be produced as mixtures of stereoisomers or as individual R- and S-stereoisomers. The individual stereoisomers may be obtained by using an optically active starting material, by resolving a racemic or non-racemic mixture of an intermediate at some appropriate stage of the synthesis, or by resolving the compounds of Formulas I–V. It is understood that the compounds of Formulas I–V encompass individual stereoisomers as well as mixtures (racemic and non-racemic) of stereoisomers. Preferably, S-stereoisomers are used in the pharmaceutical compositions and methods of the present invention.

Synthesis of Pyrrolidine Derivatives

The compounds of formulas I to V may be prepared by a variety of synthetic sequences that utilize established chemical transformations. The general pathway to the present compounds is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain intermediates compounds. These intermediates are then reacted with a variety of alcohols, amides, or protected amino acid residues to obtain the propyl esters and amides of the invention.

methyl(triphenyl-phosphoranylidene)acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

SCHEME II

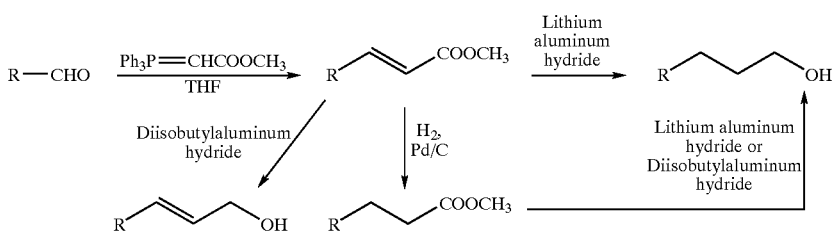

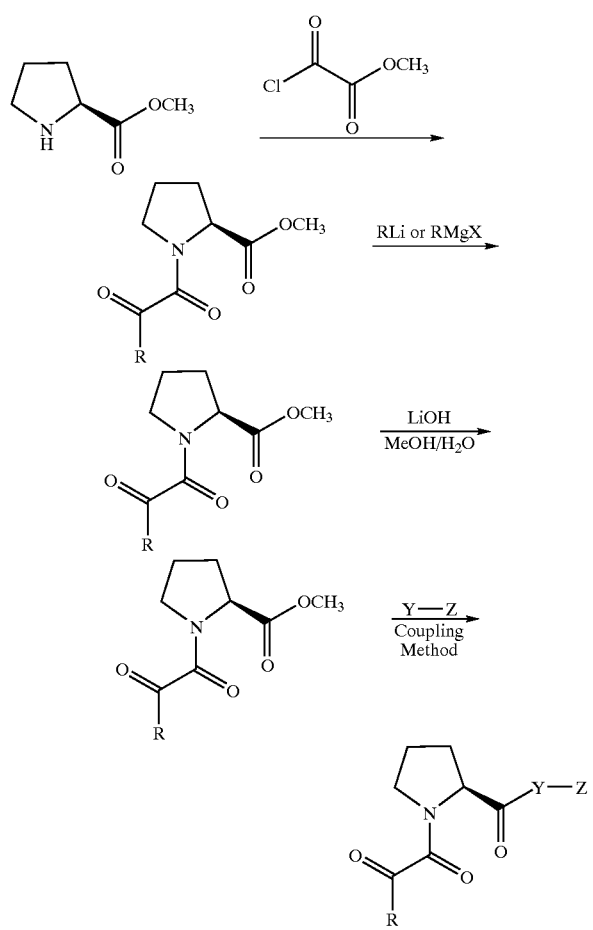

SCHEME I

The substituted alcohols may be prepared by a number of methods known to those skilled in the art of organic synthesis. As described in Scheme II, alkyl or aryl aldehydes may be homologated to phenyl propanols by reaction with Longer chain alcohols may be prepared by homologation of benzylic and higher aldehydes. Alternatively, these aldehydes may be prepared by conversion of the corresponding phenylacetic and higher acids, and phenethyl and higher alcohols.

Affinity for FKBP12

The compounds used in the inventive methods and pharmaceutical compositions preferably have an affinity for the FK506 binding protein, particularly FKBP12. The inhibition of the prolyl peptidyl cis-trans isomerase activity of FKBP may be measured as an indicator of this affinity.

$K_i$ Test Procedure

Inhibition of the peptidyl-prolyl isomerase (rotamase) activity of the compounds used in the inventive methods and pharmaceutical compositions can be evaluated by known methods described in the literature (Harding et al., Nature, 1989, 341:758–760; Holt et al. J. Am. Chem. Soc., 115:9923–9938). These values are obtained as apparent $K_i$'s and are presented for representative compounds in TABLE I.

The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 ml of ice cold assay buffer (25 mM HEPES, pH 7.8, 100 mM NaCl), 10 ml of FKBP (2.5 mM in 10 mM Tris-Cl pH 7.5, 100 mM NaCl, 1 mM dithiothreitol), 25 ml of chymotrypsin (50 mg/ml in 1 mM HCl) and 10 ml of test compound at various concentrations in dimethyl sulfoxide. The reaction is initiated by the addition of 5 ml of substrate (succinyl-Ala-Phe-Pro-Phe-para-nitroanilide, 5 mg/ml in 2.35 mM LiCl in trifluoroethanol).

The absorbance at 390 nm versus time is monitored for 90 seconds using a spectrophotometer and the rate constants are determined from the absorbance versus time data files.

TABLE I

In Vitro Test Results - Formulas I to V

| No. | Z | R₁ | $K_i$ |
|---|---|---|---|
| 1 | 1,1-dimethylpropyl | 3-phenylpropyl | 42 |
| 2 | " | 3-phenyl-prop-2-(E)-enyl | 125 |
| 3 | " | 3-(3,4,5-trimethoxy-phenyl)propyl | 200 |
| 4 | " | 3-(3,4,5-trimethoxy-phenyl)-prop-2-(E)-enyl | 65 |
| 5 | " | 3-(4,5-methylenedioxy)-phenylpropyl | 170 |
| 6 | " | 3-(4,5-methylenedioxy)phenylprop-2-(E)-enyl | 160 |
| 7 | " | 3-cyclohexylpropyl | 200 |
| 8 | " | 3-cyclohexylprop-2-(E)-enyl | 600 |
| 9 | " | (1R)-1,3-diphenyl-1-propyl | 52 |
| 10 | 2-furanyl | 3-phenylpropyl | 4000 |
| 11 | 2-thienyl | " | 92 |
| 12 | 2-thiazolyl | " | 100 |
| 13 | phenyl | " | 1970 |
| 14 | 1,1-dimethylpropyl | 3-(2,5-dimethoxy)phenylpropyl | 250 |
| 15 | " | 3-(2,5-dimethoxy)phenylprop-2-(E)-enyl | 450 |
| 16 | " | 2-(3,4,5-trimethoxyphenyl)ethyl | 120 |
| 17 | " | 3-(3-pyridyl)propyl | 5 |
| 18 | " | 3-(2-pyridyl)propyl | 195 |
| 19 | " | 3-(4-pyridyl)propyl | 23 |
| 20 | cyclohexyl | 3-phenylpropyl | 82 |
| 21 | tert-butyl | " | 95 |
| 22 | cyclohexylethyl | " | 1025 |
| 23 | cyclohexylethyl | 3-(3-pyridyl)propyl | 1400 |
| 24 | tert-butyl | 3-(3-pyridyl)propyl | 3 |
| 25 | 1,1-dimethylpropyl | 3,3-diphenylpropyl | 5 |
| 26 | cyclohexyl | 3-(3-pyridyl)propyl | 9 |
| 27 | 2-thienyl | 3-(3-pyridyl)propyl | 1000 |
| 28 | tert-butyl | 3,3-diphenylpropyl | 5 |
| 29 | cyclohexyl | " | 20 |
| 30 | 2-thienyl | 3,3-diphenylpropyl | 150 |

Route of Administration

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Other routes of administration known in the pharmaceutical art are also contemplated by this invention.

Dosage

Dosage levels on the order of about 0.1 mg to about 10,000 mg of the active ingredient compound are useful in the treatment of the above conditions, with preferred levels of about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful. The considerations for determining the proper dose levels are well known in the art.

The compounds can be administered with other hair revitalizing agents. Specific dose levels for the other hair revitalizing agents will depend upon the factors previously stated and the effectiveness of the drug combination.

EXAMPLES

The following examples are illustrative of the present invention and are not intended to be limitations thereon. Unless otherwise indicated, all percentages are based upon 100% by weight of the final composition.

Example 1

Synthesis of (2S)-2-({1-oxo-5-phenyl}-pentyl-1-(3,3-dimethyl-1,2-dioxopentyl)pyrrolidine (2S)-2-1-oxo-4-phenylbutyl-N-benzylpyrrolidine 1-chloro-4-phenylbutane (1.78 g; 10.5 mmol) in 20 ml of THF was added to 0.24 g (10 mmol) of magnesium turnings in 50 ml of refluxing THF. After the addition was complete, the mixture was refluxed for an additional 5 hours, and then added slowly to a refluxing solution of N-benzyl-L-proline ethyl ester (2.30 g (10 mmol) in 100 ml of THF. After 2 hours of further reflux, the mixture was cooled and treated with 5 ml of 2 N HCl. The reaction mixture was diluted with ether (100 ml) and washed with saturated NaHCO₃, water and brine. The organic phase was dried, concentrated and chromatographed, eluting with 5:1 CH₂Cl₂:EtOAc to obtain 2.05 g (64%) of the ketone as an oil. $^1$H NMR (CDCl₃; 300 MHz): 1.49–2.18 (m, 8H); 2.32–2.46 (m, 1H); 2.56–2.65 (m, 2H); 2.97–3.06 (m, 1H); 3.17–3.34 (m, 1H); 3.44–3.62 (m, 1H); 4.02–4.23 (m, 2H); 7.01–7.44 (m, 10H).

(2S)-2-(1-oxo-4-phenyl)butylpyrrolidine

The ketone compound (500 mg) and palladium hydroxide (20% on carbon, 50 mg) was hydrogenated at 40 psi in a Paar shaker overnight. The catalyst was removed by filtration and the solvent was removed in vacuo. The free amine was obtained as a yellow oil (230 mg; 100%). $^1$H NMR (CDCl₃; 300 MHz): 1.75–2.34 (m, 10H); 2.55 (m, 2H); 2.95 (dm, 1H); 3.45–3.95 (m, 1H); 4.05 (m, 1H); 7.37 (m, 5H).

(2S)-2-(1-oxo-4-phenyl)butyl-1-(1,2-dioxo-2-methoxyethyl)pyrrolidine

To a solution of (2S)-2-(1-oxo-4-phenyl)butylpyrrolidine (230 mg; 1.0 mmol) in CH₂Cl₂ (20 ml) at 0° C. was added dropwise methyloxalyl chloride (135 mg; 1.1 mmol). After stirring at 0° C. for 3 hours, the reaction was quenched with saturated NH₄Cl and the organic phase was washed with water and brine and dried and concentrated. The crude residue was purified on a silica gel column, eluting with 20:1 CH₂Cl₂:EtOAc to obtain 300 mg of the oxamate as a clear oil (98%). $^1$H NMR (CDCl₃; 300 MHz): 1.68 (m, 4H); 1.91–2.38 (m, 4H); 2.64 (t, 2H); 3.66–3.80 (m, 2H); 3.77, 3.85 (s, 3H total); 4.16 (m, 2H); 4.90 (m, 1H); 7.16 (m, 3H); 7.27 (m, 2H).

(2S)-2-({1-oxo-5-phenyl}-pentyl-1-(3,3-dimethyl-1,2-dioxopentyl)pyrrolidine

To a solution of the oxamate above (250 mg; 0.79 mmol) in anhydrous ether (15 ml), cooled to −78° C., was added 1,1-dimethylpropyl-magnesium chloride (0.8 ml of a 1.0 M solution in ether; 0.8 mmol). After stirring the resulting mixture at −78° C. for 2 hours, the reaction was quenched by the addition of 2 ml of saturated NH₄Cl, followed by 100 ml of EtOAc. The organic phase was washed with brine, dried, concentrated, and purified on a silica gel column, eluting with 50:1 $CH_2Cl_2$:EtOAc. The compound was obtained as a clear oil, 120 mg. $^1$H NMR ($CDCl_3$, 300 MHz): δ 0.87 (t, 3H, J=7.5); 1.22 (s, 3H); 1.25 (s, 3H); 1.67 (m, 4H); 1.70–2.33 (m, 6H); 2.61 (t, 2H, J=7.1); 3.52 (m, 2H); 4.17 (t, 2H, J=6.2); 4.52 (m, 1H); 7.16–7.49 (m, 5H). Analysis calculated for $C_{22}H_{31}NO_3$—$H_2O$: C, 70.37; H, 8.86; N, 3.73. Found: 70.48; H, 8.35; N, 3.69.

Example 2

Synthesis of 2-phenyl-1-ethyl 1-(3,3-dimethyl-1,2-dioxopentyl)-2-piperidinecarbothioate Methyl (2S)-1-(1,2-dioxo-2-methoxyethyl)-2-pyrrolidinecarboxylate A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 ml) was added dropwise. The resulting mixture was stirred at 0° C. for 1,5 hour. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR ($CDCl_3$): δ 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Methyl (2S)-1-(1,2-dioxo-3,3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 ml of tetrahydrofuran (THF) was cooled to −78° C. and treated with 14.2 ml of a 1.0 M solution of 1,1-dimethylpropylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR ($CDCl_3$): δ 0.88 (t, 3H); 1.22, 1.26 (s, 3H each); 1.75(dm, 2H); 1.87–2.10 (m, 3H); 2.23 (m, 1H); 3.54 (m, 2H); 3.76 (s, 3H); 4.52 (dm, 1H, J=8.4, 3.4).

(2S)-1-(1,2-dioxo-3,3-dimethylpentyl)-2-pyrrolidinecarboxylic acid

A mixture of methyl (2S)-1-(1,2-dioxo-3,3-dimethylpentyl)-2-pyrrolidinecarboxylate (2.10 g; 8.23 mmol), 1 N LiOH (15 ml), and methanol (50 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 1.73 g (87%) of snow-white solid which did not require further purification. $^1$H NMR ($CDCl_3$): δ 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

2-phenyl-1-ethyl 1-(3,3-dimethyl-1,2-dioxopentyl)-2-piperidinecarbothioate

To a solution of (2S)-1-(1,2-dioxo-3,3-dimethylpentyl)-2-pyrrolidinecarboxylic acid (241 mg; 1.0 mmol) in $CH_2Cl_2$ (10 ml) was added dicyclohexylcarbo-diimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of $CH_2Cl_2$. The mixture was allowed to warm to room temperature with stirring overnight. The solids were removed by filtration and the filtrate was concentrated in vacuo; the crude residue was purified by flash chromatography (10:1 hexane:EtOAc) to obtain 302 mg (84%) of the compound as an oil. $^1$H NMR ($CDCl_3$, 300 MHz): δ 0.85 (t, 3H, J=7.5); 1.29 (s, 3H); 1.31 (s, 3H); 1.70–2.32 (m, 6H); 2.92 (t, 2H, J=7.4); 3.22 (t, 2H, J=7.4); 3.58 (m, 2H); 4.72 (m, 1H); 7.23–7.34 (m, 5H). Analysis calculated for $C_{20}H_{27}NO_3S$ —0.4 $H_2O$: C, 65.15; H, 7.60; N, 3.80. Found: C, 65.41; H, 7.49; N, 3.72.

Example 3

Synthesis of 2-phenyl-1-ethyl (2S)-1-(3,3-dimethyl-1,2-dioxopentyl)-2-pyrrolidinecarbothioate Methyl 1-(1,2-dioxo-2-methoxyethyl)-2-piperidinecarboxylate A solution of methyl pipecolate hydrochloride (8.50 g; 47.31 mmol) in dry methylene chloride (100 ml) was cooled to 0° C. and treated with triethylamine (10.5 g; 103 mmol; 2.1 eq). After stirring the formed slurry under a nitrogen atmosphere for 15 minutes, a solution of methyl oxalyl chloride (8.50 g; 69.4 mmol) in methylene chloride (75 ml) was added dropwise. The resulting mixture was stirred at 0° C. for 1,5 hours. After filtering to remove solids, the organic phase was washed with water, dried over $MgSO_4$ and concentrated. The crude residue was purified on a silica gel column, eluting with 50% ethyl acetate in hexane, to obtain 9.34 g (86%) of the product as a reddish oil. Mixture of cis-trans amide rotamers; data for trans rotamer given. $^1$H NMR ($CDCl_3$): δ 1.22–1.45 (m, 2H); 1.67–1.78 (m, 3H); 2.29 (m, 1H); 3.33 (m, 1H); 3.55 (m, 1H); 3.76 (s, 3H); 3.85, 3.87 (s, 3H total); 4.52 (dd, 1H).

Methyl 1-(1,2-dioxo-3,3-dimethylpentyl)-2-piperidinecarboxylate

A solution of methyl 1-(1,2-dioxo-2-methoxyethyl)-2-piperidinecarboxylate (3.80 g; 16.57 mmol) in 75 ml of tetrahydrofuran (THF) was cooled to −78° C. and treated with 20.7 ml of a 1.0 M solution of 1,1-dimethylpropylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 3.32 g (74%) of the oxamate as a colorless oil. $^1$H NMR ($CDCl_3$): δ 0.88 (t, 3H); 1.21, 1.25 (s, 3H each); 1.35–1.80 (m, 7H); 2.35 (m, 1H); 3.24 (m, 1H); 3.41 (m, 1H); 3.76 (s, 3H); 5.32 (d, 1H)

1-(1,2-dioxo-3,3-dimethylpentyl)-2-piperidinecarboxylic acid

A mixture of methyl 1-(1,2-dioxo-3,3-dimethylpentyl)-2-piperidinecarboxylate (3.30 g; 12.25 mmol), 1 N LiOH (15 ml), and methanol (60 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 2.80 g (87%) of snow-white solid which did not require further purification. $^1$H NMR ($CDCl_3$): δ 0.89 (t, 3H); 1.21, 1.24 (s, 3H each); 1.42–1.85 (m, 7H); 2.35 (m, 1H) 3.22 (d, 1H); 3.42 (m, 1H); 5.31 (d, 1H).

2-phenyl-1-ethyl (2S)-1-(3,3-dimethyl-1,2-dioxopentyl)-2-pyrrolidinecarbothioate To a solution of 1-(1,2-dioxo-3,3-dimethylpentyl)-2-piperidine-carboxylic acid (255 mg; 1.0 mmol) in $CH_2Cl_2$ (10 ml) was added dicyclohexylcarbodiimide (226 mg; 1.1 mmol). After stirring the resulting mixture for 5 minutes, the solution was cooled to 0° C. and treated with a solution of phenyl mercaptan (138 mg; 1.0 mmol) and 4-dimethylaminopyridine (6 mg) in 5 ml of $CH_2Cl_2$. The mixture was allowed to warm to room temperature with stirring overnight. The solids were removed by filtration and the filtrate was concentrated in vacuo; the crude residue was purified by flash chromatography (10:1 hexane:EtOAc) to obtain 300 mg (80%) of the compound as an oil. $^1H$ NMR ($CDCl_3$, 300 MHz): d 0.94 (t, 3H, J=7.5); 1.27 (s, 3H); 1.30 (s, 3H); 1.34–1.88 (m, 7H); 2.45 (m, 1H); 2.90 (t, 2H, J=7.7); 3.26 (t, 2H, J=7.7); 3.27 (m, 1H); 3.38 (m, 1H); 5.34 (m, 1H); 7.24–7.36 (m, 5H). Analysis calculated for $C_{21}H_{29}NO_3S$: C, 67.17; H, 7.78; N, 3.73. Found: C, 67.02; H, 7.83; N, 3.78.

Example 4

Synthesis of 3-phenyl-1-propyl (2S)-1-(3,3-dimethyl-1,2-dioxopentyl)-2-(4-thiazolidine) carboxylate 1-(1,2-dioxo-2-methoxyethyl)2-(4-thiazolidine)-carboxylate A solution of L-thioproline (1.51 g; 11.34 mmol) in 40 ml of dry methylene chloride was cooled to 0° C. and treated with 3.3 ml (2.41 g; 23,81 mmol) of triethylamine. After stirring this mixture for 30 minutes, a solution of methyl oxalyl chloride (1.81 g; 14.74 mmol) was added dropwise. The resulting mixture was stirred at 0° C. for 1.5 hours, filtered through Celite to remove solids, dried and concentrated. The crude material was purified on a silica gel column, eluting with 10% MeOH in methylene chloride, to obtain 2.0 g of the oxamate as an orange-yellow solid.

3-phenyl-1-propyl (2S)-1-(1,2-dioxo-2-methoxyethyl)2-(4-thiazolidine)carboxylate 1-(1,2-dioxo-2-methoxyethyl)2-(4-thiazolidine)-carboxylate (500 mg; 2.25 mmol), 3-phenyl-1-propanol (465 mg; 3.42 mmol), dicyclohexylcarbodiimide (750 mg; 3.65 mmol), 4-dimethylaminopyridine (95 mg; 0.75 mmol) and camphorsulfonic acid (175 mg; 0.75 mmol) in 30 ml of methylene chloride were stirred together overnight. The mixture was filtered through Celite to remove solids and chromatographed (25% ethyl acetate/hexane) to obtain 690 mg of material. $^1H$ NMR ($CDCl_3$, 300 MHz); δ 1.92–2.01 (m, 2H); 2.61–2.69 (m, 2H); 3.34 (m, 1H); 4.11–4.25 (m, 2H); 4.73 (m, 1H); 5.34 (m, 1H); 7.12 (m, 3H); 7.23 (m, 2H). 3-phenyl-1-propyl (2S)-1-(3,3-dimethyl-1,2-dioxopentyl)-2-(4-thiazolidine)carboxylate A solution of 3-phenyl-1-propyl (2S)-1-(1,2-dioxo-2-methoxyethyl)2-(4-thiazolidine)carboxylate (670 mg; 1.98 mmol) in tetrahydrofuran (10 ml) was cooled to −78° C. and treated with 2.3 ml of a 1.0 M solution of 1,1-dimethylpropylmagnesium chloride in ether. After stirring the mixture for 3 hours, it was poured into saturated ammonium chloride, extracted into ethyl acetate, and the organic phase was washed with water, dried and concentrated. The crude material was purified on a silica gel column, eluting with 25% ethyl acetate in hexane, to obtain 380 mg of the compound as a yellow oil. $^1H$ NMR ($CDCl_3$, 300 MHz): d 0.86 (t, 3H); 1.21 (s, 3H); 1.26 (s, 3H); 1.62–1.91 (m, 3H); 2.01 (m, 2H); 2.71 (m, 2H); 3.26–3.33 (m, 2H); 4.19 (m, 2H); 4.58 (m, 1H); 7.19 (m, 3H); 7.30 (m, 2H). Analysis calculated for $C_{20}H_{27}NO_4S$: C, 63.63; H, 7.23; N, 3.71. Found: C, 64.29; H, 7.39; N, 3.46.

Example 5

Synthesis of 3-(3-pyridyl)-1-propyl (2S)-1-(3,3-dimethyl-1,2-dioxopentyl)-2-(4-thiazolidine) carboxylate The compound of Example 5 was prepared according to the procedure of Example 4, using 3-(3-pyridyl)-1-propanol in the final step, to yield 3-(3-pyridyl)-1-propyl (2S)-1-(3,3-dimethyl-1,2-dioxopentyl)-2-(4-thiazolidine)carboxylate. $^1H$ NMR ($CDCl_3$, 300 MHz): δ 0.89 (t, 3H, J=7.3); 1.25 (s, 3H); 1.28 (s, 3H); 1.77 (q, 2H, J=7.3); 2.03 (tt, 2H, J=6.4, 7.5); 2.72 (t, 2H, J=7.5); 3.20 (dd, 1H, J=4.0, 11.8); 3.23 (dd, 1H, J=7.0, 11.8); 4.23 (t, 2H, J=6.4); 4.55 (d, 2H, J=8.9); 5.08 (dd, 1H, J=4.0, 7.0); 7.24 (m, 1H); 8.48 (m, 2H). Analysis calculated for $C_{19}H_{26}N_2O_4S$—0.5 $H_2O$: C, 58.89; H, 7.02; N, 7.23. Found: C, 58.83; H, 7.05; N, 7.19.

Example 6

Synthesis of 3-(3-pyridyl)-1-propyl (2S)-1-(3,3-Dimethyl-1,2-dioxopentyl)-2-pyrrolidinecarboxylate, N-oxide Methyl (2S)-1-(1,2-dioxo-2-methoxyethyl)-2-pyrrolidinecarboxylate A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 minutes, a solution of methyl oxalyl chloride (3.20 g; 26.12 mmol) in methylene chloride (45 ml) was added dropwise. The resulting mixture was stirred at 0° C. for 1.5 hour. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1H$ NMR ($CDCl_3$): δ 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Methyl (2S)-1-(1,2-dioxo-3,3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 ml of tetrahydrofuran (THF) was cooled to −78° C. and treated with 14.2 ml of a 1.0 M solution of 1,1-dimethylpropylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1H$ NMR ($CDCl_3$): δ 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

(2S)-1-(1,2-dioxo-3,3-dimethylpentyl)-2-pyrrolidinecarboxylic acid

A mixture of methyl (2S)-1-(1,2-dioxo-3,3-dimethylpentyl-2-pyrrolidine-carboxylate (2.10 g; 8.23 mmol), 1 N LiOH (15 ml), and methanol (50 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 1.73 g (87%) of snow-white solid which did not require further purification. $^1$H NMR (CDCl$_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

3-(3-Pyridyl)-1-propyl (2S)-1-(3,3-dimethyl-1,2-dioxopentyl)-2-pyrrolidinecarboxylate A mixture of (2S)-1-(1,2-dioxo-3,3-dimethylpentyl)-2-pyrrolidinecarboxylic acid (4.58 g; 19 mmol), 3-pyridinepropanol (3.91 g; 28.5 mmol), dicyclohexylcarbodiimide (6.27 g; 30.4 mmol), camphorsulfonic acid (1.47 g; 6.33 mmol) and 4-dimethyl aminopyridine (773 mg; 6.33 mmol) in methylene chloride (100 ml) was stirred overnight under a nitrogen atmosphere. The reaction mixture was filtered through Celite to remove solids and concentrated in vacuo. The crude material was triturated with several portions of ether, and the ether portions were filtered through Celite to remove solids and concentrated in vacuo. The concentrated filtrate was purified on a flash column (gradient elution, 25% ethyl acetate in hexane to pure ethyl acetate) to obtain 5.47 g (80%) of GPI 1046 as a colorless oil (partial hydrate). $^1$H NMR (CDCl$_3$, 300 MHz): δ 0.85 (t, 3H); 1.23, 1.26 (s, 3H each); 1.63–1.89 (m, 2H); 1.90–2.30 (m, 4H); 2.30–2.50 (m, 1H); 2.72 (t, 2H); 3.53 (m, 2H); 4.19 (m, 2H); 4.53 (m, 1H); 7.22 (m, 1H); 7.53 (dd, 1H); 8.45. Analysis calculated for C$_{20}$H$_{28}$NO$_4$—0.25 H$_2$O: C, 65.82; H, 7.87; N, 7.68. Found: C, 66.01; H, 7.85; N, 7.64.

3-(3-Pyridyl)-1-propyl (2S)-1-(3,3-dimethyl-1.2-dioxopentyl)-2-pyrrolidinecarboxylate, N-oxide A solution of 3-(3-pyridyl)-1-propyl (2S)-1-(3,3-dimethyl-1,2-dioxopentyl)-2-pyrrolidinecarboxylate (190 mg; 0.52 mmol) and m-chloroperbenzoic acid (160 mg of 57%–86% material, 0.53 mmol) was stirred in methylene chloride (20 ml) at room temperature for 3 hours. The reaction mixture was diluted with methylene chloride and washed twice with 1 N NaOH. The organic extract was dried and concentrated, and the crude material was chromatographed, eluting with 10% methanol in ethyl acetate, to obtain 130 mg of the Compound of Example 6. $^1$H NMR (CDCl$_3$, 300 MHz): δ 0.83 (t, 3H); 1.21 (s, 3H); 1.25 (s, 3H); 1.75–2.23 (m, 8H); 2.69 (t, 2H, J=7.5); 3.52 (t, 2H, J=6.3); 4.17 (dd, 2H, J=6.3); 4.51 (m, 1H); 7.16–7.22 (m, 2H); 8.06–8.11 (m, 2H). Analysis calculated for C$_{20}$H$_{28}$N$_2$O$_5$—0.75 H$_2$O: C, 61.60; H, 7.63; N, 7.18. Found: C, 61.79; H, 7.58; N, 7.23.

Example 7

Synthesis of 3-(3-Pyridyl)-1-propylmercaptyl 2S-1-[(2-methylbutyl)carbamoyl]pyrrolidine-2-carboxylate 3-(3-Pyridyl)-1-propylchloride To a solution of 3-(3-pyridyl)-1-propanol (10 g; 72.4 mmol) in chloroform (100 ml) was added dropwise a solution of thionyl chloride (12.9 g; 108.6 mmol) in chloroform (50 ml). The resulting mixture was refluxed for 1 hour, then poured into ice-cold 50% aqueous potassium hydroxide (150 ml). The layers were separated, and the organic phase was dried, concentrated, and purified on a silica gel column, eluting with 40% ethylacetate in hexane, to obtain 10 g (65%) of the chloride as a clear oil. $^1$H NMR (300 MHz, CDCl$_3$): δ 2.02–2.11 (m, 2H); 2.77 (m, 2H); 3.51 (m, 2H); 7.20 (m, 1H); 7.49 (m, 1H); 8.45 (m, 2H).

3-(3-Pyridyl)-1-propylmercaptan

A mixture of 3-(3-pyridyl)-1-propylchloride (3 g; 19.4 mmol) and thiourea (1.48 g; 19.4 mmol) in ethanol (10 ml) was refluxed for 24 hours. Aqueous sodium hydroxide, 15 ml of a 0.75 N solution, was added, and the mixture was refluxed for an additional 2 hours. After cooling to room temperature, the solvent was removed in vacuo. Chromatographic purification of the crude thiol on a silica gel column eluting with 50% ethyl acetate in hexane delivered 1.2 g of 3-(3-Pyridyl)-1-propylmercaptan as a clear liquid. $^1$H NMR (300 MHz, CDCl$_3$): δ 1.34 (m, 1H); 1.90 (m, 2H); 2.52 (m, 2H); 2.71 (m, 2H); 7.81 (m, 1H); 7.47 (m, 1H); 8.42 (m, 2H).

3-(3-Pyridyl)-1-propylmercaptyl N-(tert-butyloxycarbonyl)pyrrolidine-2-carboxylate A mixture of N-(tert-butyloxycarbonyl)-(S)-proline (3.0 g; 13.9 mmol); 3-(3-Pyridyl)-1-propylmercaptan (3.20 g; 20.9 mmol), dicyclohexylcarbodiimide (4.59 g; 22.24 mmol), camphorsulfonic acid (1.08 g; 4.63 mmol), and 4-dimethylaminopyridine (0.60 g; 4.63 mmol) in dry methylene chloride (100 ml) was stirred overnight. The reaction mixture was diluted with methylene chloride (50 ml) and water (100 ml), and the layers were separated. The organic phase was washed with water (3×100 ml), dried over magnesium sulfate, and concentrated, and/the crude residue was purified on a silica gel column eluting with ethyl acetate to obtain 4.60 g (95%) of the thioester as a thick oil. $^1$H NMR (300 MHz, CDCl$_3$): δ 1.45 (s, 9H); 1.70–2.05 (m, 5H); 2.32 (m, 1H); 2.71 (t, 2H); 2.85 (m, 2H); 3.50 (m, 2H); 4.18 (m, 1H); 7.24 (m, 1H); 7.51 (m, 1H); 8.48 (m, 2H).

3-(3-Pyridyl)-1-propylmercaptyl pyrrolidine-2-carboxylate

A solution of 3-(3-Pyridyl)-1-mercaptyl N-(tert-butyloxycarbonyl)pyrrolidine-2-carboxylate (4.60 g; 13.1 mmol) in methylene chloride (60 ml) and trifluoroacetic acid (6 ml) was stirred at room temperature for three hours. Saturated potassium carbonate was added until the pH was basic, and the reaction mixture was extracted with methylene chloride (3×). The combined organic extracts were dried and concentrated to yield 2.36 g (75%) of the free amine as a thick oil. $^1$H NMR (300 MHz, CDCl$_3$): δ 1.87–2.20 (m, 6H); 2.79 (m, 2H); 3.03–3.15 (m, 4H total); 3.84 (m, 1H); 7.32 (m, 1H); 7.60 (m, 1H); 8.57 (m, 2H).

3-(3-Pyridyl)-1-propylmercaptyl 2S-1-[(2-methylbutyl)carbamoyl]pyrrolidine-2-carboxylate (101)

A solution of 2-methylbutylamine (113 mg; 1.3 mmol) and triethylamine (132 mg; 1.3 mmol) in methylene chloride (5 ml) was added to a solution of triphosgene (128 mg; 0.43 mmol) in methylene chloride (5 ml). The resulting mixture was refluxed for 1 hour and then cooled to room temperature. 3-(3-Pyridyl)-1-propylmercaptyl pyrrolidine-2-carboxylate (300 mg; 1.3 mmol) in 5 ml of methylene chloride was added and the resulting mixture was stirred for 1 hour and then partitioned between water and a 1:1 mixture of ethyl acetate and hexane. The organic phase was dried, concentrated and purified by column chromatography (50% ethyl acetate/hexane) to obtain 250 mg (55%) of the compound of Example 7 as an oil. $^1$H NMR (300 MHz, CDCl$_3$): d $^1$H NMR (CDCl$_{13}$, 300 MHz) δ 0.89–0.93 (m, 6H); 1.10–1.20 (m, 1H); 1.27 (s, 1H); 1.36–1.60 (m, 2H); 1.72 (s, 2H); 1.97–2.28 (m, 6H); 2.70–2.75 (m, 2H); 2.92–3.54 (m, 6H); 4.45–4.47 (m, 1H); 7.21–7.29 (m, 1H); 7.53–7.56 (dd, 1H); 8.46–8.48 (s, 2H).

Example 8

Synthesis of 3-(3-Pyridyl)-1-propyl 2S-1-[(1', 1'-Dimethylpropyl)carbamoyl]pyrrolidine-2-carboxylate Reaction of 3-(3-pyridyl)-1-propylmercaptyl pyrrolidine-2-carboxylate with the isocyanate generated from tertamylamine and triphosgene, as described for Example 7, provided the compound of Example 8 in 62% yield. $^1$H NMR (CDCl$_3$, 300 MHz): δ 0.83 (t, 3H); 1.27 (s, 6H); 1.64–1.71 (m, 2H); 1.91–2.02 (m, 7H); 2.66–2.71 (t, 2H); 2.85 (m, 2H); 3.29–3.42 (m, 2H); 4.11 (br, 1H); 4.37–4.41 (m, 1H).

Example 9

Synthesis of 3-(3-pyridyl)-1-propylmercaptyl 2S-1-[(cyclohexyl)thiocarbamoyl]-pyrrolidine-2-carboxylate A mixture of cyclohexylisothiocyanate (120 mg; 0.9 mmol), 3-(3-pyridyl)-1-propylmercaptyl pyrrolidine-2-carboxylate (200 mg; 0.9 mmol) and triethylamine (90 mg; 0.9 mmol) in 20 ml of methylene chloride was stirred for 1 hour and then partitioned between water and a 1:1 mixture of ethyl acetate and hexane. The organic phase was dried, concentrated and purified by column chromatography (50% ethyl acetate/hexane) to obtain 160 mg (47%) of the compound of Example 9. $^1$H NMR (CDCl$_3$, 300 MHz): δ 1.16–1.40 (m, 6H); 1.50–1.71 (m, 4H); 1.95–2.08 (m, 7H); 2.70–2.75 (t, 2H); 3.03 (m, 2H); 3.40–3.60 (m, 2H); 4.95–4.98 (d, 1H); 5.26–5.29 (d, 1H); 7.17–7.25 (m, 1H).

Example 10

Synthesis of 3-(para-Methoxyphenyl)-1-propylmercaptyl(2S)-N-(benzenesulfonyl)-pyrrolidine-2-carboxylate 3-(p-Methoxyphenyl)-1-propylbromide To a solution of 3-(p-methoxyphenyl)-1-propanol (16.6 g; 0.1 mol) in 250 ml of toluene, cooled to 0° C., was added dropwise 26 ml of phosphorus tribromide (0.27 mol). Following completion of the addition, the reaction was stirred at room temperature for 1 hour, then refluxed for an additional hour. The reaction was cooled and poured onto ice, the layers were separated, and the organic phase washed with saturated sodium bicarbonate (3×) and brine (3×). The crude material obtained upon drying and evaporation of the solvent was chromatographed, eluting with 10% EtOAc/hexane, to obtain 14 g (61%) of 3-(p-methoxyphenyl)-1-propylbromide.

3-(p-Methoxyphenyl)-1-propylmercaptan

A mixture of 3-(p-methoxyphenyl)-1-propylbromide (14 g; 61 mmol) and thiourea (5.1 g; 67 mmol) in ethanol (150 ml) was refluxed for 48 hours. Evaporation of the solvent provided a clear glassy compound, which was dissolved in 50 ml of water and treated with 100 ml of 40% aqueous sodium hydroxide.

After stirring the resulting mixture for two hours, the product was extracted into ether (3×), and the combined organic extracts were washed with sodium bicarbonate and brine, dried, and concentrated.

Chromatographic purification of the crude thiol on a silica gel column eluting with 2% either in hexane delivered 10.2 g of 3-(p-methoxyphenyl)-1-propylmercaptan as a clear liquid. $^1$H NMR (300 MHz, CDCl$_3$): δ 1.34 (t, 1H); 1.88–1.92 (m, 2H); 2.49–2.53 (m, 2H); 2.64–2.69 (m, 2H); 3.77 (s, 3H); 6.80–6.84 (m, 2H); 7.06–7.24 (m, 2H).

3-(p-Methoxyphenyl)-1-mercaptyl N-(tert-butyloxycarbonyl)pyrrolidine-2-carboxylate A mixture of N-(tert-butyloxycarbonyl)-(S)-proline (2.0 g; 9.29 mmol), 3-(p-methoxyphenyl)-1-propylmercaptan (1.86 g; 10.22 mmol), 1-(3-dimethylaminopropyl)-3-ethylcarbodiimide hydrochloride (1.96 g; 10.22 mmol), and 4-dimethylaminopyridine (catalytic) in dry methylene chloride (50 ml) was stirred overnight. The reaction mixture was diluted with methylene chloride (50 ml) and water 100 (ml), and the layers were separated. The organic phase was washed with water (3×100 ml), dried over magnesium sulfate, and concentrated to provide 3.05 g of the product (100%) as a thick oil. $^1$H NMR (300 MHz, CDCl$_3$): δ 1.15 (s, 9H); 1.84–2.31 (m, 6H); 2.61 (m, 2H); 2.83 (m, 2H); 3.51 (m, 2H); 3.75 (s, 3H); 6.79 (d, 2H, J=8.04); 7.05 (m, 2H).

3-(p-Methoxyphenyl)-1-mercaptyl pyrrolidine-2-carboxylate

A solution of 3-(p-methoxyphenyl)-mercaptyl N-(tert-butyloxycarbonyl)pyrrolidine-2-carboxylate (3.0 g; 8.94 mmol) in methylene chloride (60 ml) and trifluoroacetic acid (6 ml) was stirred at room temperature for three hours. Saturated potassium carbonate was added until the pH was basic, and the reaction mixture was extracted with methylene chloride (3×). The combined organic extracts were dried and concentrated to yield 1.73 g (69%) of the free amine as a thick oil. $^1$H NMR (300 MHz, CDCl$_3$): δ 1.80–2.23 (m, 6H); 2.62 (m, 2H); 2.81 (m, 2H); 3.01 (m, 2H); 3.75 (s, 3H); 3.89 (m, 1H); 6.81 (m, 2H); 7.06 (m, 2H).

3-(para-Methoxyphenyl)-1-propylmercaptyl (2S)-N-(benzenesulfonyl)pyrrolidine-2-carboxylate A solution of 3-(p-methoxyphenyl)-1-mercaptyl pyrrolidine-2-carboxylate (567 mg; 2.03 mmol) and benzenesulfonyl chloride (358 mg; 2.03 mmol) in methylene chloride (5 ml) was treated with diisopropylethylamine (290 mg; 2.23 mmol) and stirred overnight at room temperature. The reaction mixture was filtered to remove solids and applied directly to a silica gel column, eluting with 25% ethyl acetate in hexane, to obtain 540 mg of the compound as a clear oil. $^1$H NMR (300 MHz, CDCl$_3$): δ 1.65–1.89 (m, 6H); 2.61 (t, 2H, J=7.3); 2.87 (t, 2H, J=7.6); 3.26 (m, 1H); 3.54 (m, 1H); 3.76 (s, 3H); 4.34 (dd, 1H, J=2.7, 8.6); 6.79 (d, 2H, J=8.7); 7.06 (d, 2H, J=8.6); 7.49–7.59 (m, 3H); 7.86 (dd, 2H, J=1.5, 6.8).

Example 11

Synthesis of 3-(para-Methoxyphenyl)-1-propylmercaptyl(2S)-N-(α-toluenesulfonyl) pyrrolidine-2-carboxylate A solution of 3-(p-Methoxyphenyl)-1-mercaptyl pyrrolidine-2-carboxylate (645 mg; 2.30 mmol) and α-toluenesulfonyl chloride (440 mg; 2.30 mmol) in methylene chloride (5 ml) was treated with diisopropylethylamine (330 mg; 2.53 mmol) and stirred overnight at room temperature. Purification as described for Example 10 provided the compound of Example 11 as a clear oil. $^1$H NMR (300 MHz, CDCl$_3$): δ 1.65–2.25 (m, 8H); 2.65 (t, 2H); 2.89–2.96 (m, 2H); 3.55–3.73 (m, 2H); 3.80 (s, 3H); 4.32 (s, 2H); 4.70–4.81 (m, 1H); 6.83 (d, 2H); 7.09 (d, 2H); 7.14 (m, 3H); 7.26 (m, 2H).

Example 12

Synthesis of 3-(para-Methoxyphenyl)-1-propylmercaptyl (2S)-N-(α-toluenesulfonyl) pyrrolidine-2-carboxylate A solution of 3-(p-methoxyphenyl)-1-mercaptyl pyrrolidine-2-carboxylate (567 mg; 2.30 mmol) and p-toluenesulfonyl chloride (425 mg; 2.23 mmol) in methylene chloride (5 ml) was stirred overnight at room temperature. Purification as described for Example 10 provided the compound of Example 12 as a clear oil. $^1$H NMR (300 MHz, CDCl$_3$): δ 1.67–1.94 (m, 6H); 2.40 (s, 3H); 2.61 (t, 2H, J=7.3); 2.84 (m, 2H, J=7.2); 3.22 (m, 1H); 3.52 (m, 1H);

3.76 (s, 3H); 4.32 (dd, 1H, J=2.9, 8.5); 6.79 (d, 2H, J=6.5); 7.07 (d, 2H, J=6.5); 7.29 (d, 2H, J=6.5); 7.74 (d, 2H, J=6.5).

Example 13

Synthesis of 1,5-Diphenyl-3-pentylmercaptyl N-(para-toluenesulfonyl)pipecolate

3-Phenyl-1-propanal

Oxalyl chloride (2.90 g; 2.29 mmol) in methylene chloride (50 ml), cooled to −78° C., was treated with dimethylsulfoxide (3.4 ml) in 10 ml of methylene chloride. After stirring for 5 min, 3-phenyl-1-propanol (2.72 g; 20 mmol) in 20 ml of methylene chloride was added, and the resulting mixture was stirred at −78° C. for 15 min, treated with 14 ml of triethylamine, stirred an additional 15 min, and poured into 100 ml of water. The layers were separated, the organic phase was dried and concentrated, and the crude residue was purified on a silica gel column, eluting with 10% ethyl acetate in hexane, to obtain 1.27 g (47%) of the aldehyde as a clear oil. $^1$H NMR (300 MHz, CDC$_3$): δ 2.80 (m, 2H); 2.98 (m, 2H); 7.27 (m, 5H); 9.81 (2, 1H).

1,5-Diphenyl-3-pentanol

A solution of 2-(bromoethyl)benzene (1.73 g; 9.33 mmol) in diethylether (10 ml) was added to a stirred slurry of magnesium turnings (250 mg; 10.18 mmol) in 5 ml of ether. The reaction was initiated with a heat gun, and after the addition was complete the mixture was heated on an oil bath for 30 min. 3-Phenyl-1-propanal (1.25 g; 9.33 mmol) was added in 10 ml of ether, and reflux was continued for 1 hour. The reaction was cooled and quenched with saturated ammonium chloride, extracted into 2×ethyl acetate, and the combined organic portions were dried and concentrated. Chromatographic purification on a silica gel column (10% ethyl acetate in hexane) delivered 1.42 g(63%) of the diphenyl alcohol. $^1$H NMR (300 MHz, CDCl$_3$): δ 1.84 (m, 4H); 2.61–2.76 (m, 4H); 3.65 (m, 1H); 7.19–7.29 (m, 10H).

1,5-Diphenyl-3-bromopentane

To a solution of 1,5-diphenyl-3-pentanol (1.20 g (5 mmol) and carbon tetrabromide (1.67 g; 5 mmol) in methylene chloride (20 ml) was added triphenylphosphine (1.31 g; 5 mmol) portionwise, at 0° C. After stirring at room temperature for 18 hours, the mixture was concentrated, triturated with ether, and the solids removed by filtration. The filtrate was passed through a plug of silica gel, eluting with hexane:methylene chloride, 10:1, to give 1.35 g (90%) of the bromide as an oil which was used without further purification. $^1$H NMR (300 MHz, CDCl$_3$): δ 2.11–2.18 (m, 4H); 2.73 (m, 2H); 2.86 (m, 2H); 3.95 (m, 1H); 7.16–7.30 (m, 10H).

1,5-Diphenyl-3-pentylmercaptan

Using the procedure described in Example 10 for the conversion of bromides to thiols, 1,5-diphenyl-3-bromopentane was converted to 1,5-diphenyl-3-pentylmercaptan in 35% overall yield. $^1$H NMR (300 MHz, CDCl$_3$): δ 1.79 (m, 2H); 1.98 (m, 2H); 2.71 (m, 3H); 2.80 (m, 2H); 7.16–7.28 (m, 10H).

1,5-Diphenyl-3-pentylmercaptyl N-(tert-butyloxycarbonyl)pyrrolidine-2-carboxylate A mixture of N-(tert-butyloxycarbonyl)-(S)-pipecolic acid (2.11 g; 9.29 mmol), 1,5-diphenyl-3-pentylmercaptan (2.58 g; 10.22 mmol), 1-(3-dimethylaminopropyl)-3-ethylcarbodiimide hydrochloride (1.96 g; 10.22 mmol) and 4-dimethylaminopyridine (catalytic) in dry methylene chloride (50 ml) was stirred overnight. The reaction mixture was diluted with methylene chloride (50 ml) and water (100 ml) and the layers were separated. The organic phase was washed with water (3×100 ml), dried over magnesium sulfate, and concentrated to provide 870 mg (20%) of the product as a thick oil, which was used without further purification.

1,5-Diphenyl-3-pentylmercaptyl pyrrolidine-2-carboxylate

A solution of 1,5-diphenyl-3-pentylmercaptyl N-(tert-butyloxycarbonyl)pyrrolidine-2-carboxylate (850 mg; 1.8 mmol) in methylene chloride (10 ml) and trifluoroacetic acid (1 ml) was stirred at room temperature for three hours. Saturated potassium carbonate was added until the pH was basic, and the reaction mixture was extracted with methylene chloride. The combined organic extracts were dried and concentrated to yield 480 mg (72%) of the free amine as a thick oil, which was used without further purification.

1,5-Diphenyl-3-pentylmercaptyl N-(para-toluenesulfonyl)pipecolate 1,5-Diphenyl-3-pentylmercaptyl N-(para-toluenesulfonyl)pipecolate(18) was prepared from 1,5-diphenyl-3-pentylmercaptyl pyrrolidine-2-carboxylate and para-toluenesulfonyl chloride as described for Example 12, in 65% yield. $^1$H NMR (CDCl$_3$, 300 MHz): δ 0.80 (m, 4H); 1.23–1.97 (m, 5H); 2.15 (d, 1H); 2.61–2.69 (m, 4H); 3.23 (m, 1H); 3.44 (dm, 1H); 4.27 (s, 2H); 4.53 (d, 1H, J=4.5); 5.06 (m, 1H); 7.16–7.34 (m, 15H).

Example 14

Synthesis of 3-phenyl-1-propyl (2S)-1-(3,3-dimethyl-1,2-dioxopentyl)-2-pyrrolidinecarboxylate (1)

Methyl (2S)-1-(1,2-dioxo-2-methoxyethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min, a solution of methyl oxalyl chloride (3.20 g; 26.12 mmol) in methylene chloride (45 ml) was added dropwise. The resulting mixture was stirred at 0° C. for 1.5 hour. After filtering to remove solids, the organic phase was washed with water, dried over MgSO$_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$H NMR (CDCl$_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Methyl (2S)-1-(1,2-dioxo-3,3-dimethylpentyl)-2-pyrrolidinecarboxylate

A solution of methyl (2S)-1-(1,2-dioxo-2-methoxyethyl)-2-pyrrolidinecarboxylate (2.35 g; 10.90 mmol) in 30 ml of tetrahydrofuran (THF) was cooled to −78° C. and treated with 14.2 ml of a 1.0 M solution of 1,1-dimethylpropylmagnesium chloride in THF. After stirring the resulting homogeneous mixture at −78° C. for three hours, the mixture was poured into saturated ammonium chloride (100 ml) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$H NMR (CDCl$_3$): d 0.88 (t, 3H); 1.22, 1.26 (s, 3H each); 1.75 (dm, 2H); 1.87–2.10 (m, 3H); 2.23 (m, 1H); 3.54 (m, 2H); 3.76 (s, 3H); 4.52 (dm, 1H, J=8.4, 3.4).

Synthesis of (2S)-1-(1,2-dioxo-3,3-dimethylpentyl)-2-pyrrolidinecarboxylic acid

A mixture of methyl (2S)-1-(1,2-dioxo-3,3-dimethylpentyl)-2-pyrrolidinecarboxylate (2.10 g; 8.23 mmol), 1 N LiOH (15 ml), and methanol (50 ml) was stirred at 0° C. for 30 minutes and at room temperature overnight. The mixture was acidified to pH 1 with 1 N HCl, diluted with water, and extracted into 100 ml of methylene chloride. The organic extract was washed with brine and concentrated to deliver 1.73 g (87%) of snow-white solid which did not require further purification. $^1$H NMR (CDCl$_3$): d 0.87 (t, 3H); 1.22, 1.25 (s, 3H each); 1.77 (dm, 2H); 2.02 (m, 2H); 2.17 (m, 1H); 2.25 (m, 1H); 3.53 (dd, 2H, J=10.4, 7.3); 4.55 (dd, 1H, J=8.6, 4.1).

3-Phenyl-1-propyl (2S)-1-(3,3-dimethyl-1,2-dioxopentyl)-2-pyrrolidinecarboxylate (1)

A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulfonic acid (190 mg; 0.8 mmol) and 4-dimethylaminopyridine (100 mg; 0.8 mmol) in methylene chloride (20 ml) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of the compound of Example 14 as a colorless oil. $^1$H NMR (CDCl$_3$): d 0.84 (t, 3H); 1.19 (s, 3H); 1.23 (s, 3H); 1.70 (dm, 2H); 1.98 (m, 5H); 2.22 (m, 1H); 2.64 (m, 2H); 3.47 (m, 2H); 4.14 (m, 2H); 4.51 (d, 1H); 7.16 (m, 3H); 7.26 (m, 2H).

Example 15

The method of Example 14 was utilized to prepare the following illustrative compounds:

Compound 2: 3-phenyl-1-prop-2-(E)-enyl (2S)-1-(3,3-dimethyl-1,2-dioxopentyl)-2-pyrrolidinecarboxylate, 80%. $^1$H NMR (360 MHZ, CDCl$_3$): d 0.86 (t, 3H); 1.21 (s, 3H); 1.25 (s, 3H); 1.54–2.10 (m, 5H); 2.10–2.37 (m, 1H); 3.52–3.55 (m, 2H); 4.56 (dd, 1H, J=3.8, 8.9); 4.78–4.83 (m, 2H); 6.27 (m, 1H); 6.67 (dd, 1H, J=15.9); 7.13–7.50 (m, 5H).

Compound 3: 3-(3,4,5-trimethoxyphenyl)-1-propyl (2S)-1-(3,3-dimethyl-1,2-dioxopentyl)-2-pyrrolidine-carboxylate, 61%. $^1$H NMR (CDCl$_3$): d 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H).

Compound 4: 3-(3,4,5-trimethoxyphenyl)-1-prop-2-(E)-enyl (2S)-1-(3,3-dimethyl-1,2-dioxopentyl)-2-pyrrolidine carboxylate, 66%. $^1$H NMR (CDCl$_3$): d 0.85 (t, 3H); 1.22 (s, 3H); 1.25 (s, 3H); 1.50–2.11 (m, 5H); 2.11–2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (s, 2H).

Compound 5: 3-(4,5-methylenedioxyphenyl)-1-propyl (2S)-1-(3,3-dimethyl-1,2-dioxopentyl)-2-pyrrolidine-carboxylate, 82%. $^1$H NMR (360 MHZ, CDCl$_3$): d 0.86 (t, 3H); 1.22 (s, 3H); 1.25 (s, 3H); 1.60–2.10 (m, 5H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Compound 6: 3-(4,5-methylenedioxyphenyl)-1-prop-2-(E)-enyl (2S)-1-(3,3-dimethyl-1,2-dioxopentyl)-2-pyrrolidinecarboxylate, 82%. $^1$H NMR (360 MHZ, CDCl$_3$): d 0.86 (t, 3H); 1.22 (s, 3H); 1.25 (s, 3H); 1.60–2.10 (m, 5H); 2.10–2.39 (m, 1H); 3.36–3.79 (m, 2H); 4.53 (dd, 1H, J=3.8, 8.6); 4.61–4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H).

Compound 8: 3-cyclohexyl-1-prop-2-(E)-enyl (2S)-1-(3,3-dimethyl-1-1,2-dioxopentyl)-2-pyrrolidinecarboxylate, 92%. $^1$H NMR (360 MHZ, CDCl$_3$): d 0.86 (t, 3H); 1.13–1.40 (m+2 singlets, 9H total); 1.50–1.87 (m, 8H); 1.87–2.44 (m, 6H); 3.34–3.82 (m, 2H); 4.40–4.76 (m, 3H); 5.35–5.60 (m, 1H); 5.60–5.82 (dd, 1H, J=6.5, 16).

Compound 9: (1R)-1,3-Diphenyl-1-propyl (2S)-1-(3,3-dimethyl-1,2-dioxopentyl)-2-pyrrolidinecarboxylate, 90%. $^1$H NMR (360 MHZ, CDCl$_3$): d 0.85 (t, 3H); 1.20 (s, 3H); 1.23 (s, 3H); 1.49–2.39 (m, 7H); 2.46–2.86 (m, 2H); 3.25–3.80 (m, 2H); 4.42–4.82 (m, 1H); 5.82 (td, 1H, J=1.8, 6.7); 7.05–7.21 (m, 3H); 7.21–7.46 (m, 7H).

Compound 10: 3-phenyl-1-propyl (2S)-1-(1,2-dioxo-2-[2-furanyl])ethyl-2-pyrrolidinecarboxylate, 99%. $^1$H NMR (300 MHZ, CDCl$_3$): d 1.66–2.41 (m, 6H); 2.72 (t, 2H, J=7.5); 3.75 (m, 2H); 4.21 (m, 2H); 4.61 (m, 1H); 6.58 (m, 1H); 7.16–7.29 (m, 5H); 7.73 (m, 2H).

Compound 11: 3-phenyl-1-propyl (2S)-1-(1,2-dioxo-2-[2-thienyl])ethyl-2-pyrrolidinecarboxylate, 81%. $^1$H NMR (300 MHZ, CDCl$_3$): d 1.88–2.41 (m, 6H); 2.72 (dm, 2H); 3.72 (m, 2H); 4.05 (m, 1H); 4.22 (m, 1H); 4.64 (m, 1H); 7.13–7.29 (m, 6H); 7.75 (dm, 1H); 8.05 (m, 1H).

Compound 13: 3-phenyl-1-propyl (2S)-1-(1,2-dioxo-2-phenyl)ethyl-2-pyrrolidinecarboxylate, 99%. $^1$H NMR (300 MHZ, CDCl$_3$): d 1.97–2.32 (m, 6H); 2.74 (t, 2H, J=7.5); 3.57 (m, 2H); 4.24 (m, 2H); 4.67 (m, 1H); 6.95–7.28 (m, 5H); 7.51–7.64 (m, 3H); 8.03–8.09 (m, 2H).

Compound 14: 3-(2,5-dimethoxyphenyl)-1-propyl (2S)-1-(3,3-dimethyl-1,2-dioxopentyl)-2-pyrrolidine-carboxylate, 99%. $^1$H NMR (300 MHZ, CDCl$_3$): d 0.87 (t, 3H); 1.22 (s, 3H); 1.26 (s, 3H); 1.69 (m, 2H); 1.96 (m, 5H); 2.24 (m, 1H); 2.68 (m, 2H); 3.55 (m, 2H); 3.75 (s, 3H); 3.77 (s, 3H); 4.17 (m, 2H); 4.53 (d, 1H); 6.72 (m, 3H).

Compound 15: 3-(2,5-dimethoxyphenyl)-1-prop-2-(E)-enyl (2S)-1-(3,3-dimethyl-1,2-dioxopentyl)-2-pyrrolidine-carboxylate, 99%. $^1$H NMR (300 MHZ, CDCl$_3$): d 0.87 (t, 3H); 1.22 (s, 3H); 1.26 (s, 3H); 1.67 (m, 2H); 1.78 (m, 1H); 2.07 (m, 2H); 2.26 (m, 1H); 3.52 (m, 2H); 3.78 (s, 3H); 3.80 (s, 3H); 4.54 (m, 1H); 4.81 (m, 2H); 6.29 (dt, 1H, J=15.9); 6.98 (s, 1H).

Compound 16: 2-(3,4,5-trimethoxyphenyl)-1-ethyl (2S)-1-(3,3-dimethyl-1,2-dioxopentyl)-2-pyrrolidine-carboxylate, 97%. $^1$H NMR (300 MHZ, CDCl$_3$): d 0.84 (t, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m,1H); 6.36 (s, 2H).

Compound 17: 3-(3-Pyridyl)-1-propyl (2S)-1-(3,3-dimethyl-1,2-dioxopentyl)-2-pyrrolidinecarboxylate, 80%. $^1$H NMR (CDCl$_3$, 300 MHZ): d 0.85 (t, 3H); 1.23, 1.26 (s, 3H each); 1.63–1.89 (m, 2H); 1.90–2.30 (m, 4H); 2.30–2.50 (m, 1H); 2.72 (t, 2H); 3.53 (m, 2H); 4.19 (m, 2H); 4.53 (m, 1H); 7.22 (m, 1H); 7.53 (dd, 1H); 8.45.

Compound 18: 3-(2-Pyridyl)-1-propyl (2S)-1-(3,3-dimethyl-1,2-dioxopentyl)-2-pyrrolidinecarboxylate, 88%. $^1$H NMR (CDCl$_3$, 300 MHZ): d 0.84 (t, 3H); 1.22, 1.27 (s, 3H each); 1.68–2.32 (m, 8H); 2.88 (t, 2H, J=7.5); 3.52 (m, 2H); 4.20 (m, 2H); 4.51 (m, 1H); 7.09–7.19 (m, 2H); 7.59 (m, 1H); 8.53 (d, 1H, J=4.9).

Compound 19: 3-(4-Pyridyl)-1-propyl (2S)-1-(3,3-dimethyl-1,2-dioxopentyl)-2-pyrrolidinecarboxylate, 91%. $^1$H NMR (CDCl$_3$, 300 MHZ): d 6.92–6.80 (m, 4H); 6.28 (m, 1H); 5.25 (d, 1H, J=5.7); 4.12 (m, 1H); 4.08 (s, 3H); 3.79 (s, 3H); 3.30 (m, 2H); 2.33 (m, 1H); 1.85–1.22 (m, 7H); 1.25 (s, 3H); 1.23 (s, 3H); 0.89 (t, 3H, J=7.5).

Compound 20: 3-phenyl-1-propyl (2S)-1-(2-cyclohexyl-1,2-dioxoethyl)-2-pyrrolidinecarboxylate, 91%. $^1$H NMR (CDCl$_3$, 300 MHZ): d 1.09–1.33 (m, 5H); 1.62–2.33 (m, 12H); 2.69 (t, 2H, J=7.5); 3.15 (dm, 1H); 3.68 (m, 2H); 4.16 (m, 2H); 4.53, 4.84 (d, 1H total); 7.19 (m, 3H); 7.29 (m, 2H).

Compound 21: 3-phenyl-1-propyl (2S)-1-(2-tert-butyl-1,2-dioxoethyl)-2-pyrrolidinecarboxylate, 92%. $^1$H NMR (CDCl$_3$, 300 MHZ): d 1.29 (s, 9H); 1.94–2.03 (m, 5H); 2.21 (m, 1H); 2.69 (m, 2H); 3.50–3.52 (m, 2H); 4.16 (m, 2H); 4.53 (m, 1H); 7.19 (m, 3H); 7.30 (m, 2H).

Compound 22: 3-phenyl-1-propyl (2S)-1-(2-cyclohexylethyl-1,2-dioxoethyl)-2-pyrrolidinecarboxylate, 97%. $^1$H NMR (CDCl3, 300 MHZ): d 0.88 (m, 2H); 1.16 (m, 4H); 1.43–1.51 (m, 2H); 1.67 (m, 5H); 94–2.01 (m, 6H); 2.66–2.87 (m, 4H); 3.62–3.77 (m, 2H); 4.15 (m, 2H); 4.86 (m, 1H); 7.17–7.32 (m, 5H).

Compound 23: 3-(3-pyridyl)-1-propyl (2S)-1-(2-cyclohexylethyl-1,2-dioxoethyl)-2-pyrrolidinecarboxylate, 70%. $^1$H NMR (CDCl$_3$, 300 MHZ) d 0.87 (m, 2H); 1.16 (m, 4H); 1.49 (m, 2H); 1.68 (m, 4H); 1.95–2.32 (m, 7H); 2.71 (m, 2H); 2.85 (m, 2H); 3.63–3.78 (m, 2H); 4.19 (m, 2H); 5.30 (m, 1H); 7.23 (m, 1H); 7.53 (m, 1H); 8.46 (m, 2H).

Compound 24: 3-(3-pyridyl)-1-propyl (2S)-1-(2-tert-butyl-1,2-dioxoethyl)-2-pyrrolidinecarboxylate, 83%. $^1$H NMR (CDCl$_3$, 300 MHZ): d 1.29 (s, 9H); 1.95–2.04 (m, 5H); 2.31 (m, 1H); 2.72 (t, 2H, J=7.5); 3.52 (m, 2H); 4.18 (m, 2H); 4.52 (m, 1H); 7.19–7.25 (m, 1H); 7.53 (m, 1H); 8.46 (m, 2H).

Compound 25: 3,3-diphenyl-1-propyl (2S)-1-(3,3-dimethyl-1,2-dioxopentyl)-2-pyrrolidinecarboxylate, 99%. $^1$H NMR (CDCl$_3$, 300 MHZ): d 0.85 (t, 3H); 1.21, 1.26 (s, 3H each); 1.68–2.04 (m, 5H); 2.31 (m, 1H); 2.40 (m, 2H); 3.51 (m, 2H); 4.08 (m, 3H); 4.52 (m, 1H); 7.18–7.31 (m, 10H).

Compound 26: 3-(3-pyridyl)-1-propyl (2S)-1-(2-cyclohexyl-1,2-dioxoethyl)-2-pyrrolidinecarboxylate, 88%. $^1$H NMR (CDCl$_3$, 300 MHZ): d 1.24–1.28 (m, 5H); 1.88–2.35 (m, 11H); 2.72 (t, 2H, J=7.5); 3.00–3.33 (dm, 1H); 3.69 (m, 2H); 4.19 (m, 2H); 4.55 (m, 1H); 7.20–7.24 (m, 1H); 7.53 (m, 1H); 8.47 (m, 2H).

Compound 27: 3-(3-Pyridyl)-1-propyl (2S)-N-([2-thienyl]glyoxyl)pyrrolidinecarboxylate, 49%. $^1$H NMR (CDCl$_3$, 300 MHZ): d 1.81–2.39 (m, 6H); 2.72 (dm, 2H); 3.73 (m, 2H); 4.21 (m, 2H); 4.95 (m, 1H); 7.19 (m, 2H); 7.61 (m, 1H); 7.80 (d, 1H); 8.04 (d, 1H); 8.46 (m, 2H).

Compound 28: 3,3-Diphenyl-1-propyl (2S)-1-(3,3-dimethyl-1,2-dioxobutyl)-2-pyrrolidinecarboxylate, 99%. $^1$H NMR (CDCl$_3$, 300 MHZ): d 1.27 (s, 9H); 1.96 (m, 2H); 2.44 (m, 4H); 3.49 (m, 1H); 3.64 (m, 1H); 4.08 (m, 4H); 4.53 (dd, 1H); 7.24 (m, 10H).

Compound 29: 3,3-Diphenyl-1-propyl (2S)-1-cyclohexyl glyoxyl-2-pyrrolidinecarboxylate, 91%. $^1$H NMR (CDCl$_3$, 300 MHZ): d 1.32 (m, 6H); 1.54–2.41 (m, 10H); 3.20 (dm, 1H); 3.69 (m, 2H); 4.12 (m, 4H); 4.52 (d, 1H); 7.28 (m, 10H).

Compound 30: 3,3-Diphenyl-1-propyl (2S)-1-(2-thienyl) glyoxyl-2-pyrrolidinecarboxylate, 75%. $^1$H NMR (CDCl$_3$, 300 MHZ): d 2.04 (m, 3H); 2.26 (m, 2H); 2.48 (m, 1H); 3.70 (m, 2H); 3.82–4.18 (m, 3H total); 4.64 (m, 1H); 7.25 (m, 11H); 7.76 (dd, 1H); 8.03 (m, 1H).

Example 16

General procedure for the synthesis of acrylic esters, exemplified for methyl (3,3,5-trimethoxy)-trans-cinnamate.

A solution of 3,4,5-trimethoxybenzaldehyde (5.0 g; 25.48 mmol) and methyl (triphenyl-phosphoranylidene)acetate (10.0 g; 29.91 mmol) in tetrahydrofuran (250 ml) was refluxed overnight. After cooling, the reaction mixture was diluted with 200 ml of ethyl acetate and washed with 2×200 ml of water, dried, and concentrated in vacuo. The crude residue was chromatographed on a silica gel column, eluting with 25% ethyl acetate in hexane, to obtain 5.63 g (88%) of the cinnamate as a white crystalline solid. $^1$H NMR (300 MHz; CDCl$_3$): d 3.78 (s, 3H); 3.85 (s, 6H); 6.32 (d, 1H, J=16); 6.72 (s, 2H); 7.59 (d, 1H, J=16).

Example 17

General procedure for the synthesis of saturated alcohols from acrylic esters, exemplified for (3,4,5-trimethoxy) phenylpropanol.

A solution of methyl (3,3,5-trimethoxy)-trans-cinnamate (1.81 g; 7.17 mmol) in tetrahydrofuran (30 ml) was added in a dropwise manner to a solution of lithium aluminum hydride (14 mmol) in THF (35 ml), with stirring and under an argon atmosphere. After the addition was complete, the mixture was heated to 75° C. for 4 hours. After cooling, it was quenched by the careful addition of 15 ml of 2 N NaOH followed by 50 ml of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil. $^1$H NMR (300 MHz; CDCl$_3$): d 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

Example 18

General procedure for the synthesis of trans-allylic alcohols from acrylic esters, exemplified for (3,4,5-trimethoxy) phenylprop-2-(E)-enol.

A solution of methyl (3,3,5-trimethoxy)-trans-cinnamate (1.35 g; 5.35 mmol) in toluene (25 ml) was cooled to –10° C. and treated with a solution of diisobutylaluminum hydride in toluene (11.25 ml of a 1.0 M solution; 11.25 mmol). The reaction mixture was stirred for 3 hours at 0° C. and then quenched with 3 ml of methanol followed by 1 N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil. $^1$H NMR (360 MHz; CDCl$_3$): d 3.85 (s, 3H); 3.87 (s, 6H); 4.32 (d, 2H, J=5.6); 6.29 (dt, 1H, J=15. 8, 5.7), 6.54 (d, 1H, J=15.8); 6.61 (s, 2H).

Example 19

In vivo Hair Generation Tests with C57 Black 6 Mice

Figure 2:
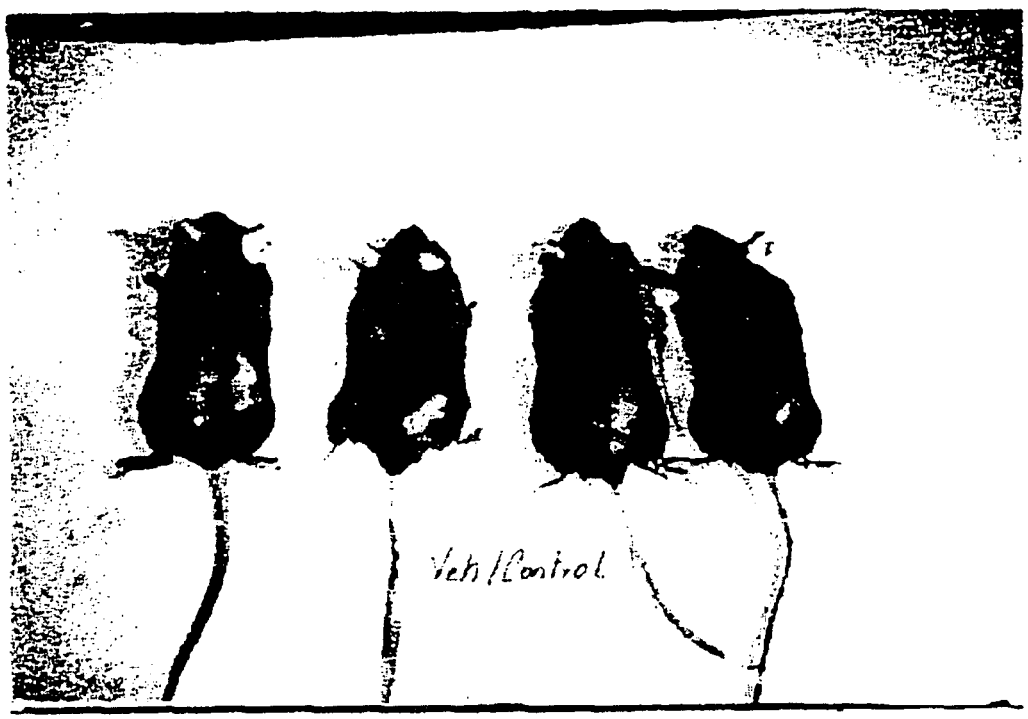
FIG. 2 is a photograph of mice treated with a vehicle after six weeks.
Figure 3:
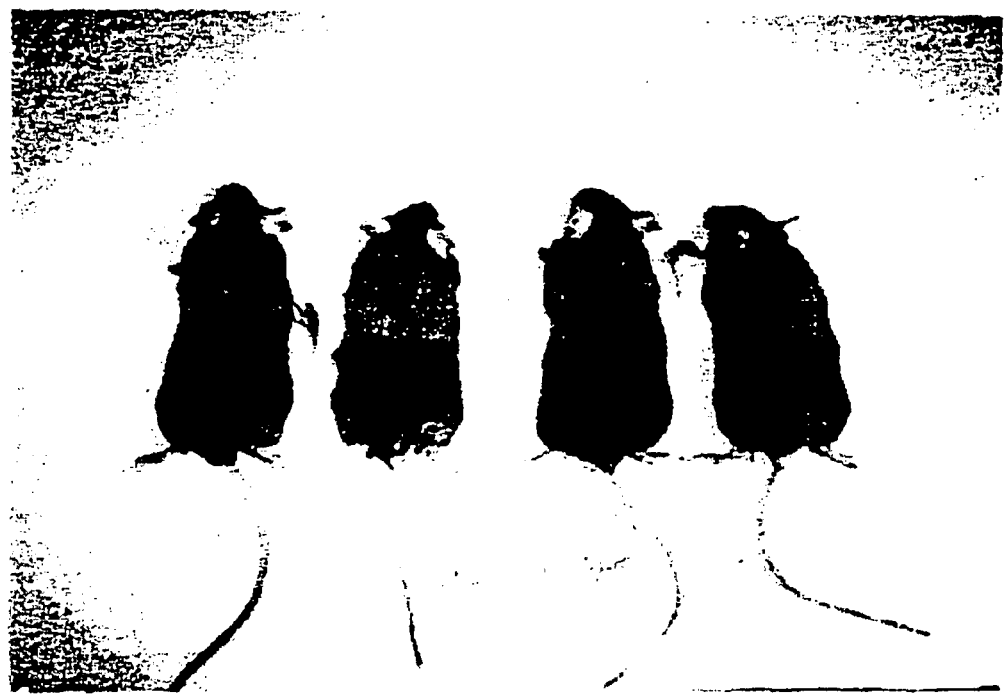
FIG. 3 is a photograph of mice treated with 10 $\mu$M of GPI 1046 after six weeks.
Figure 4:
FIG. 4 is a photograph of mice treated with 30 $\mu$M of GPI 1046 after six weeks.

Experiment A: C57 black 6 mice were used to demonstrate the hair revitalizing properties of a pyrrolidine derivative, GPI 1046. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIGS. 2, 3 and 4, four animals per group were treated by topical administration with 20% propylene glycol vehicle (FIG. 2), 10 μM GPI 1046 (FIG. 3) or 30 μM GPI 1046 (FIG. 4) dissolved in the vehicle. The animals were treated with vehicle or GPI 1046 every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle exhibited only a small amount of hair growth in patches or tufts, with less than 3% of the shaved area covered with new growth. In contrast, FIG. 3 shows that animals treated with 10 µM GPI 1046 exhibited dramatic hair growth, covering greater than 90% of the shaved area in all animals. Further, FIG. 4 shows that mice treated with 30 µM GPI 1046 exhibited essentially complete hair regrowth and their shaved areas were indistinguishable from unshaven C57 black 6 mice.

Experiment B: C57 Black 6 mice were used to demonstrate the hair revitalizing properties of various compounds of the present invention and other related low molecular weight, small molecule compounds. C57 Black 6 mice, 55 to 75 days old, had an area of about 2 inches by 2 inches on their hindquarters shaved to remove all existing hair. Care was taken not to nick or cause abrasion to the underlying dermal layers. The animals were in anagen growth phase when shaved. Five animals per group were treated by topical administration with a vehicle, FK506, a pyrrolidine derivative of the present invention (GPI 1046), or another low molecular weight, small molecule compound (GPI 1605, GPI 1312, GPI 1572, GPI 1389, GPI 1511, or GPI 1234) to the shaved area. The animals were treated three times per week, and hair growth was evaluated 14 days after initiation of treatment. Hair growth was quantitated by the percent of shaved area covered by new hair growth, as scored by a blinded observer, on a scale of 0 (no growth) to 5 (complete hair regrowth in shaved area).

FIG. 5 shows that after 14 days, the animals treated with vehicle exhibited the beginning of hair growth in small tufts. By contrast, most of the animals treated with the low molecular weight, small molecule pyrrolidine derivatives of the present invention and other related compounds exhibited dramatic hair growth.

Example 20

A lotion comprising the following composition may be prepared.

|  | (%) |
|---|---|
| 95% Ethanol | 80.0 |
| a pyrrolidine derivative | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added a pyrrolidine derivative, α-tocopherol acetate, ethylene oxide (40 mole) adducts of hardened castor oil, perfume and a dye. The resulting mixture is stirred and dissolved, and purified water is added to the mixture to obtain a transparent liquid lotion.

5 ml of the lotion may be applied once or twice per day to a site having marked baldness or alopecia.

Example 21

A lotion comprising the following composition shown may be prepared.

|  | (%) |
|---|---|
| 95% Ethanol | 80.0 |
| a pyrrolidine derivative | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added a pyrrolidine derivative, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 22

An emulsion may be prepared from A phase and B phase having the following compositions.

|  | (%) |
|---|---|
| (A phase) |  |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| a pyrrolidine derivative | 0.01 |
| (B phase) |  |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to four times per day to a site having marked baldness or alopecia.

Example 23

A cream may be prepared from A phase and B phase having the following compositions.

|  | (%) |
|---|---|
| (A Phase) |  |
| Fluid paraffin | 5.0 |
| Cetostearyl alcohol | 5.5 |
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) |  |
| a pyrrolidine derivative | 0.8 |
| Glycerine | 7.0 |

-continued

|  | (%) |
| --- | --- |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 24

A liquid comprising the following composition may be prepared.

|  | (%) |
| --- | --- |
| Polyoxyethylene butyl ether | 20.0 |
| Ethanol | 50.0 |
| a pyrrolidine derivative | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, a pyrrolidine derivative, and perfume. The resulting mixture is stirred, and purified water is added to the mixture to obtain a liquid.

The liquid may be applied once to 4 times per day to a site having marked baldness or alopecia.

Example 25

A shampoo comprising the following composition may be prepared.

|  | (%) |
| --- | --- |
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| a pyrrolidine derivative | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethyl-aminoacetate. Then a mixture obtained by adding 5.0 g of a pyrrolidine derivative, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 26

A patient is suffering from alopecia senilis. A pyrrolidine derivative or a pharmaceutical composition comprising the same may be administered to the patient. Increased hair growth is expected to occur following treatment.

Example 27

A patient is suffering from male pattern alopecia. A pyrrolidine derivative or a pharmaceutical composition comprising the same may be administered to the patient. Increased hair growth is expected to occur following treatment.

Example 28

A patient is suffering from alopecia areata. A pyrrolidine derivative or a pharmaceutical composition comprising the same may be administered to the patient. Increased hair growth is expected to occur following treatment.

Example 29

A patient is suffering from hair loss caused by skin lesions. A pyrrolidine derivative or a pharmaceutical composition comprising the same may be administered to the patient. Increased hair growth is expected to occur following treatment.

Example 30

A patient is suffering from hair loss caused by tumors. A pyrrolidine derivative or a pharmaceutical composition comprising the same may be administered to the patient. Increased hair growth is expected to occur following treatment.

Example 31

A patient is suffering from hair loss caused by a systematic disorder, such as a nutritional disorder or an internal secretion disorder. A pyrrolidine derivative or a pharmaceutical composition comprising the same may be administered to the patient. Increased hair growth is expected to occur following treatment.

Example 32

A patient is suffering from hair loss caused by chemotherapy. A pyrrolidine derivative or a pharmaceutical composition comprising the same may be administered to the patient. Increased hair growth is expected to occur following treatment.

Example 33

A patient is suffering from hair loss caused by radiation. A pyrrolidine derivative or a pharmaceutical composition comprising the same may be administered to the patient. Increased hair growth is expected to occur following treatment.

The invention being thus described, it will be obvious that the same may be varied in many ways. Such variations are not to be regarded as a departure from the spirit and scope of the invention and all such modifications are intended to be included within the scope of the following claims.

We claim:
1. A pharmaceutical composition which comprises:
(i) an effective amount of a compound of formula I

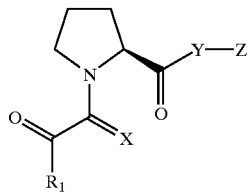

or a pharmaceutically acceptable salt, ester, or solvate thereof, for treating alopecia or promoting hair growth in an animal in need thereof, wherein:
$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$;
wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;
$Ar_1$ and $Ar_2$ are independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;
X is O, S, $CH_2$, or two hydrogen atoms;
Y is O or $NR_2$;
$R_2$ is hydrogen or $C_1$–$C_6$ alkyl;
Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, $C_1$–$C_6$ straight or branched chain alkyl substituted with $C_3$–$C_8$ cycloalkyl, and $C_2$–$C_6$ straight or branched chain alkenyl substituted with $C_3$–$C_8$ cycloalkyl,
or Z is the fragment

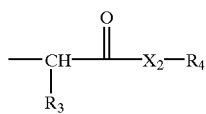

wherein:
$R_3$ is $C_1$–$C_9$ straight or branched chain alkyl which is unsubstituted or substituted with $C_3$–$C_8$ cycloalkyl or $Ar_1$;
$X_2$ is O or $NR_5$;
$R_5$ is selected from the group consisting of hydrogen, $C_1$–$C_6$ straight or branched chain alkyl, and $C_2$–$C_6$ straight or branched chain alkenyl; and
$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl;

(ii) a hair revitalizing agent; and
(iii) a pharmaceutically acceptable carrier.
2. The pharmaceutical composition of claim 1, wherein Z and $R_1$ are lipophilic.
3. The pharmaceutical composition of claim 1, wherein the compound is selected from the group consisting of:
3-phenyl-1-propyl (2S)-1-(3,3-dimethyl-1,2-dioxopentyl)-2-pyrrolidinecarboxylate;
3-phenyl-1-prop-2-(E)-enyl (2S)-1-(3,3-dimethyl-1,2-dioxopentyl)-2-pyrrolidinecarboxylate;
3-(3,4,5-trimethoxyphenyl)-1-propyl (2S)-1-(3,3-dimethyl-1,2-dioxopentyl)-2-pyrrolidinecarboxylate;
3-(3,4,5-trimethoxyphenyl)-1-prop-2-(E)-enyl (2S)-1-(3,3-dimethyl-1,2-dioxopentyl)-2-pyrrolidinecarboxylate;
3-(4,5-dichlorophenyl)-1-propyl (2S)-1-(3,3-dimethyl-1,2-dioxopentyl)-2-pyrrolidinecarboxylate;
3-(4,5-dichlorophenyl)-1-prop-2-(E)-enyl (2S)-1-(3,3-dimethyl-1,2-dioxopentyl)-2-pyrrolidinecarboxylate;
3-(4,5-methylenedioxyphenyl)-1-propyl (2S)-1-(3,3-dimethyl-1,2-dioxopentyl)-2-pyrrolidinecarboxylate;
3-(4,5-methylenedioxyphenyl)-1-prop-2-(E)-enyl (2S)-1-(3,3-dimethyl-1,2-dioxopentyl)-2-pyrrolidinecarboxylate;
3-cyclohexyl-1-propyl (2S)-1-(3,3-dimethyl-1,2-dioxopentyl)-2-pyrrolidinecarboxylate;
3-cyclohexyl-1-prop-2-(E)-enyl (2S)-1-(3,3-dimethyl-1,2-dioxopentyl)-2-pyrrolidinecarboxylate;
(1R)-1,3-diphenyl-1-propyl (2S)-1-(3,3-dimethyl-1,2-dioxopentyl)-2-pyrrolidinecarboxylate;
(1R)-1,3-diphenyl-1-prop-2-(E)-enyl (2S)-1-(3,3-dimethyl-1,2-dioxopentyl)-2-pyrrolidinecarboxylate;
(1R)-1-cyclohexyl-3-phenyl-1-propyl (2S)-1-(3,3-dimethyl-1,2-dioxopentyl)-2-pyrrolidinecarboxylate;
(1R)-1-cyclohexyl-3-phenyl-1-prop-2-(E)-enyl (2S)-1-(3,3-dimethyl-1,2-dioxopentyl)-2-pyrrolidinecarboxylate;
(1R)-1-(4,5-dichlorophenyl)-3-phenyl-1-propyl (2S)-1-(3,3-dimethyl-1,2-dioxopentyl)-2-pyrrolidinecarboxylate;
3-phenyl-1-propyl (2S)-1-(1,2-dioxo-2-cyclohexyl)ethyl-2-pyrrolidinecarboxylate;
3-phenyl-1-propyl (2S)-1-(1,2-dioxo-4-cyclohexyl)butyl-2-pyrrolidinecarboxylate;
3-phenyl-1-propyl (2S)-1-(1,2-dioxo-2-[2-furanyl])ethyl-2-pyrrolidinecarboxylate;
3-phenyl-1-propyl (2S)-1-(1,2-dioxo-2-[2-thienyl])ethyl-2-pyrrolidinecarboxylate;
3-phenyl-1-propyl (2S)-1-(1,2-dioxo-2-[2-thiazolyl])ethyl-2-pyrrolidinecarboxylate;
3-phenyl-1-propyl (2S)-1-(1,2-dioxo-2-phenyl)ethyl-2-pyrrolidinecarboxylate;
1,7-diphenyl-4-heptyl (2S)-1-(3,3-dimethyl-1,2-dioxopentyl)-2-pyrrolidinecarboxyate;
3-phenyl-1-propyl (2S)-1-(3,3-dimethyl-1,2-dioxo-4-hydroxybutyl)-2-pyrrolidinecarboxylate;
3-phenyl-1-propyl (2S)-1-(3,3-dimethyl-1,2-dioxopentyl)-2-pyrrolidinecarboxamide;
1-[1-(3,3-dimethyl-1,2-dioxopentyl)-L-proline]-L-phenylalanine ethyl ester;
1-[1-(3,3-dimethyl-1,2-dioxopentyl)-L-proline]-L-leucine ethyl ester;
1-[1-(3,3-dimethyl-1,2-dioxopentyl)-L-proline]-L-phenylglycine ethyl ester;

1-[1-(3,3-dimethyl-1,2-dioxopentyl)-L-proline]-L-phenylalanine phenyl ester;

1-[1-(3,3-dimethyl-1,2-dioxopentyl)-L-proline]-L-phenylalanine benzyl ester; and 1-[1-(3,3-dimethyl-1,2-dioxopentyl)-L-proline]-L-isoleucine ethyl ester;

or a pharmaceutically acceptable salt, ester, or solvate thereof.

4. A pharmaceutical composition which comprises:

(i) an effective amount of a compound of formula II

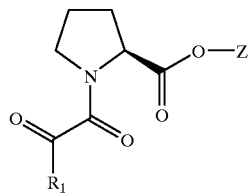

II or a pharmaceutically acceptable salt, ester, or solvate thereof, for treating alopecia or promoting hair growth in an animal in need thereof, wherein:

$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl or $Ar_1$, wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

Z is $C_1$–$C_6$ straight or branched chain alkyl, or $C_2$–$C_6$ straight or branched chain alkenyl, wherein said Z is substituted with one or more substituent(s) independently selected from the group consisting of $Ar_1$, $C_3$–$C_8$ cycloalkyl, $C_1$–$C_6$ straight or branched chain alkyl substituted with $C_3$–$C_8$ cycloalkyl, and $C_2$–$C_6$ straight or branched chain alkenyl substituted with $C_3$–$C_8$ cycloalkyl, or Z is the fragment

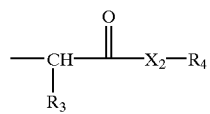

wherein:

$R_3$ is $C_1$–$C_9$ straight or branched chain alkyl which is unsubstituted or substituted with $C_3$–$C_8$ cycloalkyl or $Ar_1$;

$X_2$ is O or $NR_5$;

$R_5$ is selected from the group consisting of hydrogen, $C_1$–$C_6$ straight or branched chain alkyl, and $C_2$–$C_6$ straight or branched chain alkenyl; and $R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl;

(ii) a hair revitalizing agent; and (iii) a pharmaceutically acceptable carrier.

5. The pharmaceutical composition of claim 4, wherein $R_1$ is selected from the group consisting of $C_1$–$C_9$ straight or branched chain alkyl, 2-cyclohexyl, 4-cyclohexyl, 2-furanyl, 2-thienyl, 2-thiazolyl, and 4-hydroxybutyl.

6. The pharmaceutical composition of claim 4, wherein Z and $R_1$ are lipophilic.

7. A pharmaceutical composition which comprises:

(i) an effective amount of a compound of formula III

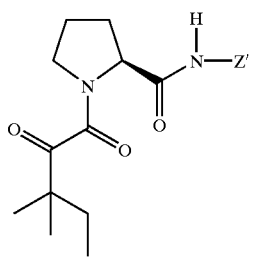

III or a pharmaceutically acceptable salt, ester, or solvate or hydrate thereof, for treating alopecia or promoting hair growth in an animal in need thereof, wherein:

Z' is the fragment

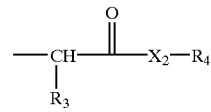

wherein:

$R_3$ is $C_1$–$C_9$ straight or branched chain alkyl or unsubstituted $Ar_1$, wherein said alkyl is unsubstituted or substituted with $C_3$–$C_8$ cycloalkyl or $Ar_1$;

$X_2$ is O or $NR_5$;

$R_5$ is selected from the group consisting of hydrogen, $C_1$–$C_6$ straight or branched chain alkyl, and $C_2$–$C_6$ straight or branched chain alkenyl;

$R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl; and $Ar_1$ is independently selected from the group consisting of 1-naphthyl, 2-naphthyl, 2-indolyl, 3-indolyl, 2-furyl, 3-furyl, 2-thienyl, 3-thienyl, 2-pyridyl, 3-pyridyl, 4-pyridyl and phenyl, wherein said $Ar_1$ is unsubstituted or substituted with one or more substituent(s) independently selected from the group consisting of hydrogen, halo, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, and amino;

(ii) a hair revitalizing agent; and (iii) a pharmaceutically acceptable carrier.

8. The pharmaceutical composition of claim 7, wherein Z' is lipophilic.

9. A pharmaceutical composition which comprises:
(i) an effective amount of a compound of formula IV

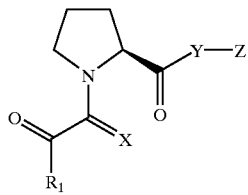

IV or a pharmaceutically acceptable salt, ester, or solvate thereof, for treating alopecia or promoting hair growth in an animal in need thereof, wherein:
$R_1$ is $C_1$–$C_6$ straight or branched chain alkyl, $C_2$–$C_6$ straight or branched chain alkenyl, $C_3$–$C_6$ cycloalkyl or $Ar_1$,
wherein said alkyl or alkenyl is unsubstituted or substituted with $C_3$–$C_6$ cycloalkyl or $Ar_2$;
$Ar_1$ and $Ar_2$ are independently selected from the group consisting of 2-furyl, 2-thienyl, and phenyl;
X is selected from the group consisting of oxygen and sulfur;
Y is oxygen;
Z is $C_1$–$C_6$ straight or branched chain alkyl or $C_2$–$C_6$ straight or branched chain alkenyl,
wherein said Z is substituted with one or more substituent(s) independently selected from the group consisting of 2-furyl, 2-thienyl, $C_3$–$C_6$ cycloalkyl, pyridyl, and phenyl, each having one or more substituent(s) independently selected from the group consisting of hydrogen and $C_1$–$C_4$ alkoxy;
(ii) a hair revitalizing agent; and
(iii) a pharmaceutically acceptable carrier.

10. The pharmaceutical composition of claim 9, wherein Z and $R_1$ are lipophilic.

11. The pharmaceutical composition of claim 9, wherein the compound is selected from the group consisting of:
3-(2,5-dimethoxyphenyl)-1-propyl (2S)-1-(3,3-dimethyl-1,2-dioxopentyl)-2-pyrrolidinecarboxylate;
3-(2,5-dimethoxyphenyl)-1-prop-2-(E)-enyl (2S)-1-(3,3-dimethyl-1,2-dioxopentyl)-2-pyrrolidinecarboxylate;
2-(3,4,5-trimethoxyphenyl)-1-ethyl (2S)-1-(3,3-dimethyl-1,2-dioxopentyl)-2-pyrrolidinecarboxylate;
3-(3-pyridyl)-1-propyl (2S)-1-(3,3-dimethyl-1,2-dioxopentyl)-2-pyrrolidinecarboxylate;
3-(2-pyridyl)-1-propyl (2S)-1-(3,3-dimethyl-1,2-dioxopentyl)-2-pyrrolidinecarboxylate;
3-(4-pyridyl)-1-propyl (2S)-1-(3,3-dimethyl-1,2-dioxopentyl)-2-pyrrolidinecarboxylate;
3-phenyl-1-propyl (2S)-1-(2-tert-butyl-1,2-dioxoethyl)-2-pyrrolidinecarboxylate;
3-phenyl-1-propyl (2S)-1-(2-cyclohexyl ethyl-1,2-dioxoethyl)-2-pyrrolidinecarboxylate;
3-(3-pyridyl)-1-propyl (2S)-1-(2-cyclohexylethyl-1,2-dioxoethyl)-2-pyrrolidinecarboxylate;
3-(3-pyridyl)-1-propyl (2S)-1-(2-tert-butyl-1,2-dioxoethyl)-2-pyrrolidinecarboxylate;
3,3-diphenyl-1-propyl (2S)-1-(3,3-dimethyl-1,2-dioxopentyl)-2-pyrrolidinecarboxylate;
3-(3-pyridyl)-1-propyl (2S)-1-(2-cyclohexyl-1,2-dioxoethyl)-2-pyrrolidinecarboxylate;
3-(3-pyridyl)-1-propyl (2S)-N-([2-thienyl]glyoxyl) pyrrolidinecarboxylate;
3,3-diphenyl-1-propyl (2S)-1-(3,3-dimethyl-1,2-dioxobutyl)-2-pyrrolidinecarboxylate;
3,3-diphenyl-1-propyl (2S)-1-cyclohexylglyoxyl-2-pyrrolidinecarboxylate; and
3,3-diphenyl-1-propyl (2S)-1-(2-thienyl)glyoxyl-2-pyrrolidinecarboxylate;
or a pharmaceutically acceptable salt, ester, or solvate thereof.

12. The pharmaceutical composition of claim 11, wherein the compound is selected from the group consisting of:
3-(3-pyridyl)-1-propyl (2S)-1-(3,3-dimethyl-1,2-dioxopentyl)-2-pyrrolidinecarboxylate;
3-(2-pyridyl)-1-propyl (2S)-1-(3,3-dimethyl-1,2-dioxopentyl)-2-pyrrolidinecarboxylate; and
3-(3-pyridyl)-1-propyl (2S)-1-(2-cyclohexyl-1,2-dioxoethyl)-2-pyrrolidinecarboxylate;
or a pharmaceutically acceptable salt, ester, or solvate thereof.

13. The pharmaceutical composition of claim 12, wherein the compound is 3-(3-pyridyl)-1-propyl (2S)-1-(3,3-dimethyl-1,2-dioxopentyl)-2-pyrrolidinecarboxylate, or a pharmaceutically acceptable salt, ester, or solvate or hydrate thereof.

14. The pharmaceutical composition of claim 1, wherein the compound is an N-glyoxyl prolyl ester.

15. A pharmaceutical composition which comprises:
i) an effective amount of a compound of formula V

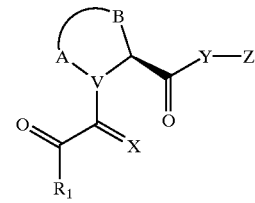

V or a pharmaceutically acceptable salt, ester, or solvate thereof, for treating alopecia or promoting hair growth in an animal in need thereof, wherein:
V is CH or N;
A and B, taken together with V and the carbon atom to which they are respectively attached, form a 5–7 membered saturated or unsaturated heterocyclic ring containing one or more heteroatom(s) selected from the group consisting of O, S, SO, $SO_2$, N, NH, and NR;
R is $C_1$–$C_9$ straight or branched chain alkyl, $C_2$–$C_9$ straight or branched chain alkenyl, $C_3$–$C_9$ cycloalkyl, $C_5$–$C_7$ cycloalkenyl, or $Ar_1$;
wherein said R is either unsubstituted of substituted with one or more substituent(s) independently selected from the group consisting of halo, haloalkyl, carbonyl, carboxy, hydroxy, nitro, trifluoromethyl, $C_1$–$C_6$ straight or branched chain alkyl, $C_2$–$C_6$ straight or branched chain alkenyl, $C_1$–$C_4$ alkoxy, $C_2$–$C_4$ alkenyloxy, phenoxy, benzyloxy, thioalkyl, alkylthio, sulfhydryl, amino, alkylamino, aminoalkyl, aminocarboxyl, and $Ar_2$;
$R_1$ is $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, or $Ar_1$,
wherein said $R_1$ is unsubstituted or substituted with one or more substituents independently selected from the group consisting of $C_1$–$C_6$ alkyl, $C_2$–$C_6$ alkenyl, $C_3$–$C_8$ cycloalkyl, $C_5$–$C_7$ cycloalkenyl, hydroxy, and $Ar_2$;

$Ar_1$ and $Ar_2$ are independently an alicyclic or aromatic, mono-, bi- or tricyclic, carbo- or heterocyclic ring, wherein the ring is either unsubstituted or substituted with one or more substituent(s), wherein the individual ring size is 5–8 members, wherein said heterocyclic ring contains 1–6 heteroatom(s) independently selected from the group consisting of O, N, and S;

X is O, S, $CH_2$, or two hydrogen atoms;

Y is O or $NR_2$;

$R_2$ is hydrogen or $C_1$–$C_6$ alkyl;

Z is $C_1$–$C_6$ straight or branched chain alkyl or $C_2$–$C_6$ straight or branched chain alkenyl, wherein said Z is substituted with one or more substituent(s) independently selected from the group consisting of $Ar_1$, $C_3$–$C_8$ cycloalkyl, $C_1$–$C_6$ straight or branched chain alkyl substituted with $C_3$–$C_8$ cycloalkyl, and $C_2$–$C_6$ straight or branched chain alkenyl, or Z is the fragment

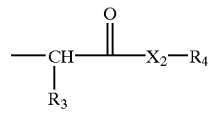

wherein:

$R_3$ is $C_1$–$C_9$ straight or branched chain alkyl which is unsubstituted or substituted with $C_3$–$C_8$ cycloalkyl or $Ar_1$;

$X_2$ is O or $NR_5$;

$R_5$ is selected from the group consisting of hydrogen, $C_1$–$C_6$ straight or branched chain alkyl, and $C_2$–$C_6$ straight or branched chain alkenyl; and $R_4$ is selected from the group consisting of phenyl, benzyl, $C_1$–$C_5$ straight or branched chain alkyl, $C_2$–$C_5$ straight or branched chain alkenyl, $C_1$–$C_5$ straight or branched chain alkyl substituted with phenyl, and $C_2$–$C_5$ straight or branched chain alkenyl substituted with phenyl;

(ii) a hair revitalizing agent; and (iii) a pharmaceutically acceptable carrier.

* * * * *